US007883897B2

(12) United States Patent
Beck et al.

(10) Patent No.: US 7,883,897 B2
(45) Date of Patent: **\*Feb. 8, 2011**

(54) METHOD FOR PRODUCING PURIFIED HEMATINIC IRON-SACCHARADIC COMPLEX AND PRODUCT PRODUCED

(75) Inventors: Robert A. Beck, Framingham, MA (US); Robert A. Mateer, Jr., North Uxbridge, MA (US)

(73) Assignee: Chromaceutical Advanced Technologies, Inc., Hopkinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/712,394

(22) Filed: Feb. 25, 2010

(65) Prior Publication Data

US 2010/0152131 A1   Jun. 17, 2010

Related U.S. Application Data

(60) Continuation of application No. 11/176,132, filed on Jul. 7, 2005, now Pat. No. 7,687,273, which is a division of application No. 10/600,173, filed on Jun. 20, 2003, now Pat. No. 6,929,954, which is a continuation-in-part of application No. 10/371,783, filed on Feb. 21, 2003, now Pat. No. 6,773,924, which is a division of application No. 09/999,394, filed on Oct. 31, 2001, now Pat. No. 6,537,820.

(60) Provisional application No. 60/245,269, filed on Nov. 2, 2000.

(51) Int. Cl.
*G01N 33/20* (2006.01)
*A61K 31/295* (2006.01)

(52) U.S. Cl. .................... 436/84; 436/8; 436/73; 436/94; 252/408.1; 514/23; 514/184; 514/502

(58) Field of Classification Search ............. 436/8, 436/73, 74, 84, 94, 174, 175, 177, 178; 252/408.1; 514/23, 53, 184, 502

See application file for complete search history.

(56) References Cited

U.S. PATENT DOCUMENTS

| | | | |
|---|---|---|---|
| 3,275,514 A | 9/1966 | Saltman et al. | |
| 3,367,834 A | 2/1968 | Dexter et al. | |
| 3,686,397 A | 8/1972 | Muller | |
| 3,821,192 A | 6/1974 | Montgomery et al. | |
| 3,886,267 A | 5/1975 | Dahlerg et al. | |
| 4,058,621 A | 11/1977 | Hill | |
| 4,104,078 A | 8/1978 | Barker et al. | |
| 4,180,567 A | 12/1979 | Herb | |
| 4,226,983 A | 10/1980 | Lane | |
| 4,370,476 A | 1/1983 | Usher et al. | |
| 4,749,695 A | 6/1988 | Schwengers | |
| 4,927,756 A | 5/1990 | Schwengers | |
| 5,160,726 A | 11/1992 | Josephson et al. | |
| 5,624,668 A | 4/1997 | Lawrence et al. | |
| 5,746,999 A | 5/1998 | Gries et al. | |
| 5,837,716 A | 11/1998 | Hough | |
| 6,372,715 B1 | 4/2002 | Kaltwasser et al. | |
| 6,537,820 B2 | 3/2003 | Beck et al. | |
| 6,651,009 B1 | 11/2003 | Trainoff et al. | |
| 6,773,924 B2 | 8/2004 | Beck et al. | |
| 6,929,954 B2 | 8/2005 | Beck et al. | |
| 6,939,715 B2 | 9/2005 | Beck et al. | |
| 7,179,939 B2 * | 2/2007 | Rangisetty et al. | 562/587 |
| 7,674,780 B2 * | 3/2010 | Newton et al. | 514/53 |
| 7,687,273 B2 * | 3/2010 | Beck et al. | 436/84 |
| 2003/0078266 A1 | 4/2003 | Kararli et al. | |
| 2005/0037996 A1 | 2/2005 | Beck et al. | |

FOREIGN PATENT DOCUMENTS

| | | |
|---|---|---|
| EP | 444194 | 9/1991 |
| ES | 8401770 | 3/1984 |
| JP | 63119691 | 5/1988 |
| JP | 1080261 | 3/1989 |
| WO | 99/07401 | 2/1999 |

OTHER PUBLICATIONS

Burger et al. "A Novel Polynuclear Iron (III) Mixed Ligand Complex for Use in Parenteral Iron Therapy," Inorganica Chimica Acta, vol. 80, pp. 231-235, 1983.

Zapsalis, C. and R.A. Beck, 1985, "Food Chemistry and Nutritional Biochemistry," Chapter 6, John Wiley & Sons, pp. 315-321.

(Continued)

*Primary Examiner*—Maureen M Wallenhorst
(74) *Attorney, Agent, or Firm*—Lerner, David, Littenberg, Krumholz & Mentlik, LLP

(57) ABSTRACT

A method for separating and purifying the active hematinic species (AHS) present in iron-saccharidic compositions, including AHS such as sodium ferric gluconate complex, ferric hydroxide-sucrose complex and ferric saccharate complex and others of similar form and function. The method separates the AHS from one or more excipients and, preferably, lyophilizes the separated AHS. Separation of the AHS permits its analytical quantification, further concentration, purification and/or lyophilization as well as preparation of new and useful products and pharmaceutical compositions, including those useful for the treatment of humans and animals.

23 Claims, 10 Drawing Sheets

OTHER PUBLICATIONS

"Raising the Bar for Quality Drugs," Chemical and Engineering News, American Chemical Society, Mar. 19, 2001, pp. 26-31.

"Principles of Food Science," edited by O.R. Fennema, "Part II, Physical Principals of Food Preservation," M. Karel et al., pp. 237-263, Marcel Dekker, Inc. 1975.

Encyclopedia of Food Science, edited by M.S. Peterson et al.,"Water Activity in Relation to Food," D.H. Chou, pp. 852-857, AVI Publ. Co., Inc., 1978.

Smales, C.M., D.S. Pepper and D.C. James, 2000, "Mechanisms of protein modification during model antiviral heat-treatment bioprocessing of beta-lactoglobulin variant A in the presence of sucrose," Biotechnol. Appl. Biochem., Oct., 32 (Pt. 2) 109-119, Oct. 2000.

Hodge, J.E. and E.M. Osman, 1976, Chapter 3, in "Food Chemistry," O.R. Fennema Ed., Marcel Dekkar, New York, pp. 92-96.

Dreywood, R., "Qualitative Test for Carbohydrate Material," Indus. and Eng. Chem. Anal. Ed., 18:499 (1946).

Hodge, J.E. and B.T. Hofreiter, "Determination of Reducing Sugars and Carbohydrates," Methods and Carbohydrate Chem., 1:384-394 (1962).

Zapsalis, C. and R.A. Beck, "Food Chemistry and Nutrional Biochemistry," Chapter 6, John Wiley & Sons, pp. 353-354 (1985.

Wyatt, P., "Light scattering and absolute characterization of macromolecules," Analytica Chimica Acta. (1993) 272:1-40.

"Freeze Drying," van Nostrand's Scientific Encyclopedia, Eighth Ed., pp. 1382-1342, 1995.

Rao et al., "Fe(III) Complexes of D-Glucose and D-Fructose," Biometals, vol. 7, pp. 1382-1342.

Geetha et al., "Transition-Metal Saccharide Chemistry: Synthesis, Spectroscopy, Electrochemistry and Magnetic Susceptibility Studies of Iron(III) Complexes of Mono- and Disaccharides," Carbohydrate Research., vol. 271, pp. 163-175, 1995.

Rao et al., "Solution of Stability of Iron-Saccharide Complexes," Bioorganic and Medicinal Chemistry Letters, vol. 2, No. 9, pp. 997-1002, 1992.

Rao et al., "Transition Metal Saccharide Chemistry and Biology: Syntheses, Characterization Solution Stability and Putative Bio-relevant Studies of Iron-Saccharide Complexes," Inorganica Chemica Acta., vol. 297, pp. 373-382, Jan. 2000.

Geiser et al.,"Structure/Histotoxicity Relationship of Parenteral Iron Preperation", Arzneimeittel Forschung. Drug Research, vol. 42, No. 12, pp. 1439-1452, 1992.

"Ferrlecit" 'Online!, Feb. 18, 1999, URL:http://www.fda.gov/cder/foi/label/1999/20955lbl.pdf.

Muller, "Classification and properties of Iron Preparation", Arzneimittel Forschung, Jun. 1974, vol. 24, No. 6, pp. 880-883.

Principles of Food Science, edited by O.R. Fennema, "Part II, Physical Principals of Food Preservation," M. Karel et al., pp. 237-263, Marcel Dekker, Inc. 1975.

Zapsalis, C. and R.A. Beck, 1985, "Food Chemistry and Nutritional Biochemistry," Chapter 10, John Wiley & Sons, pp. 588-591.

Zapsalis, C. and R.A. Beck, Food Chemistry and Nutritional Biochemistry, 1985, Chapter 1, pp. 23-26.

Tonkovic et al., "Inorganica Chimica Acta", 80:251, 1983.

* cited by examiner

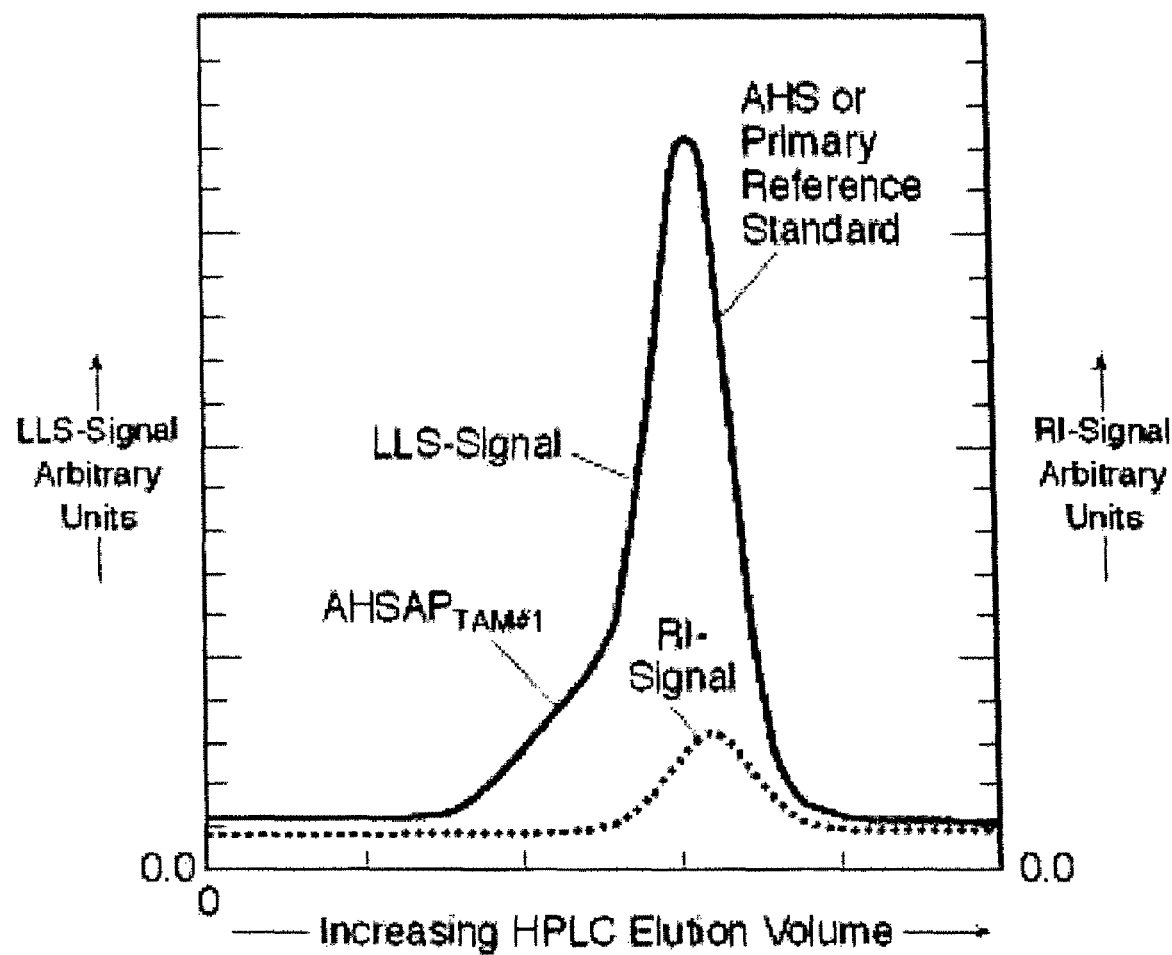

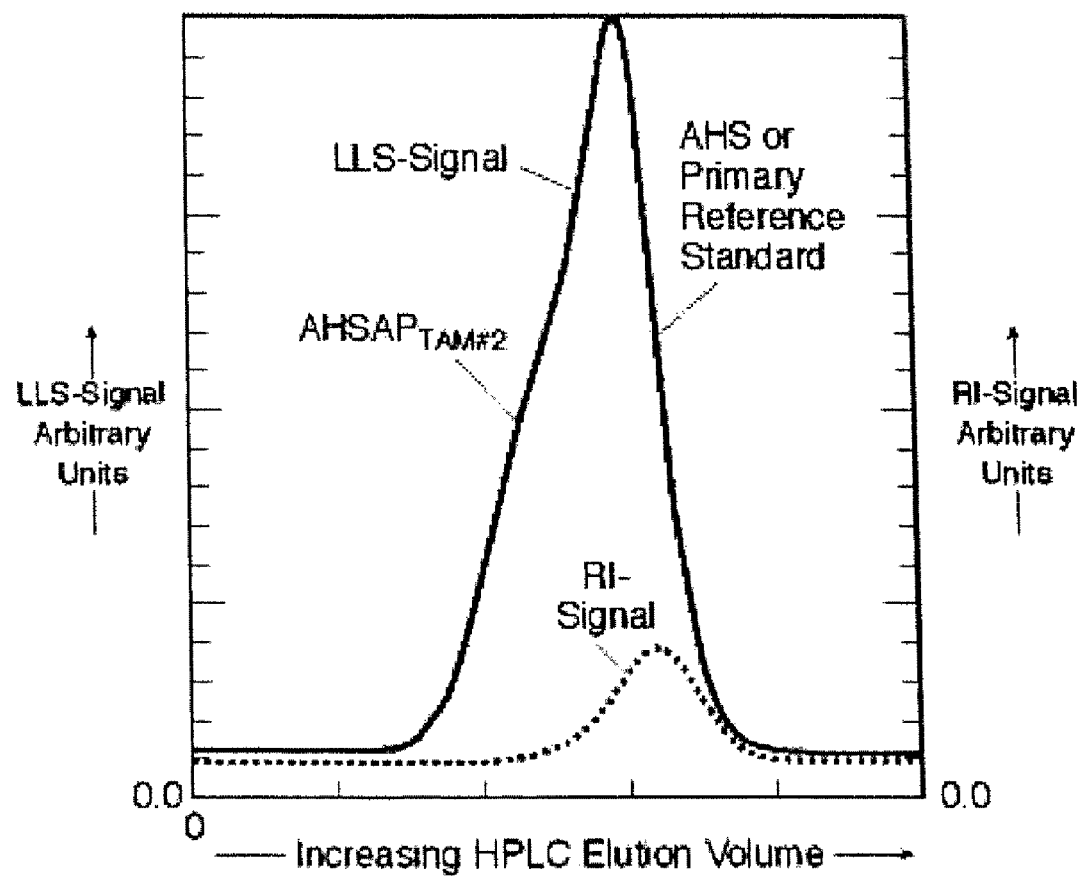

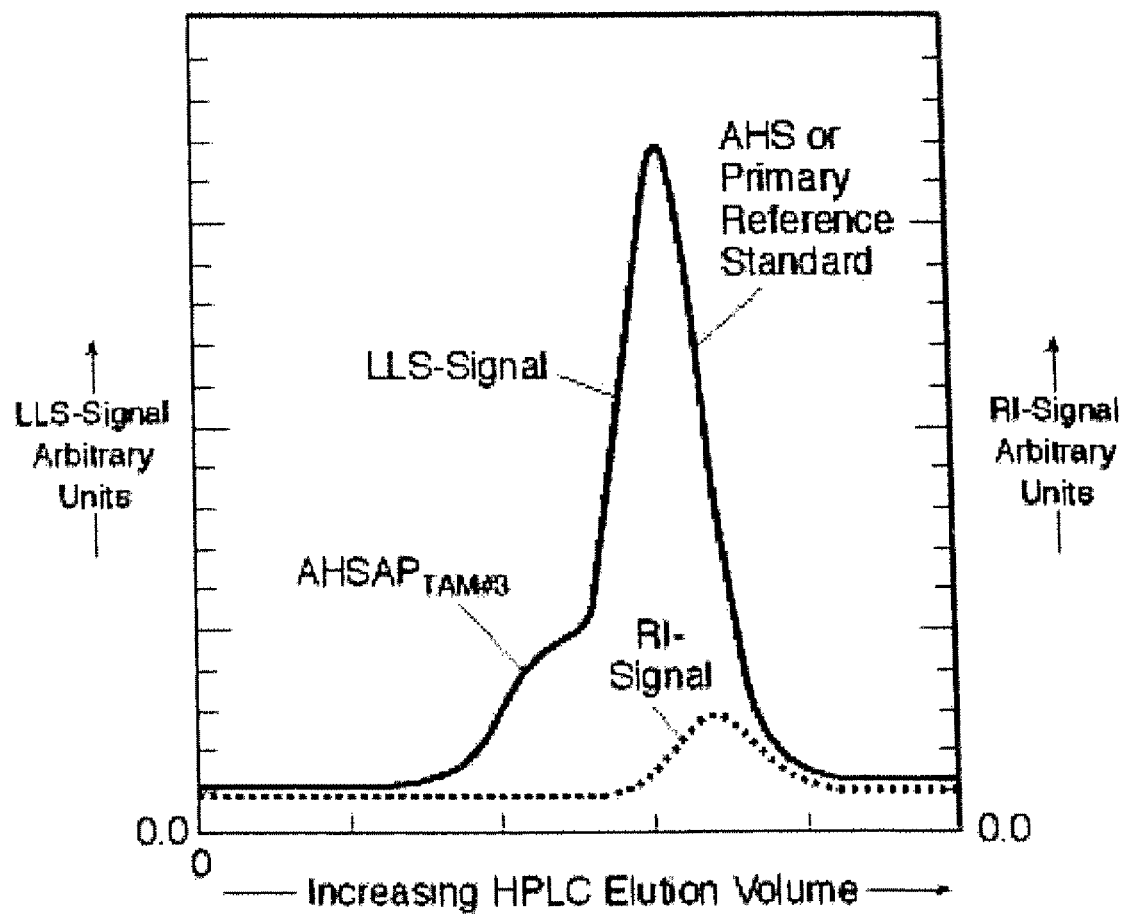

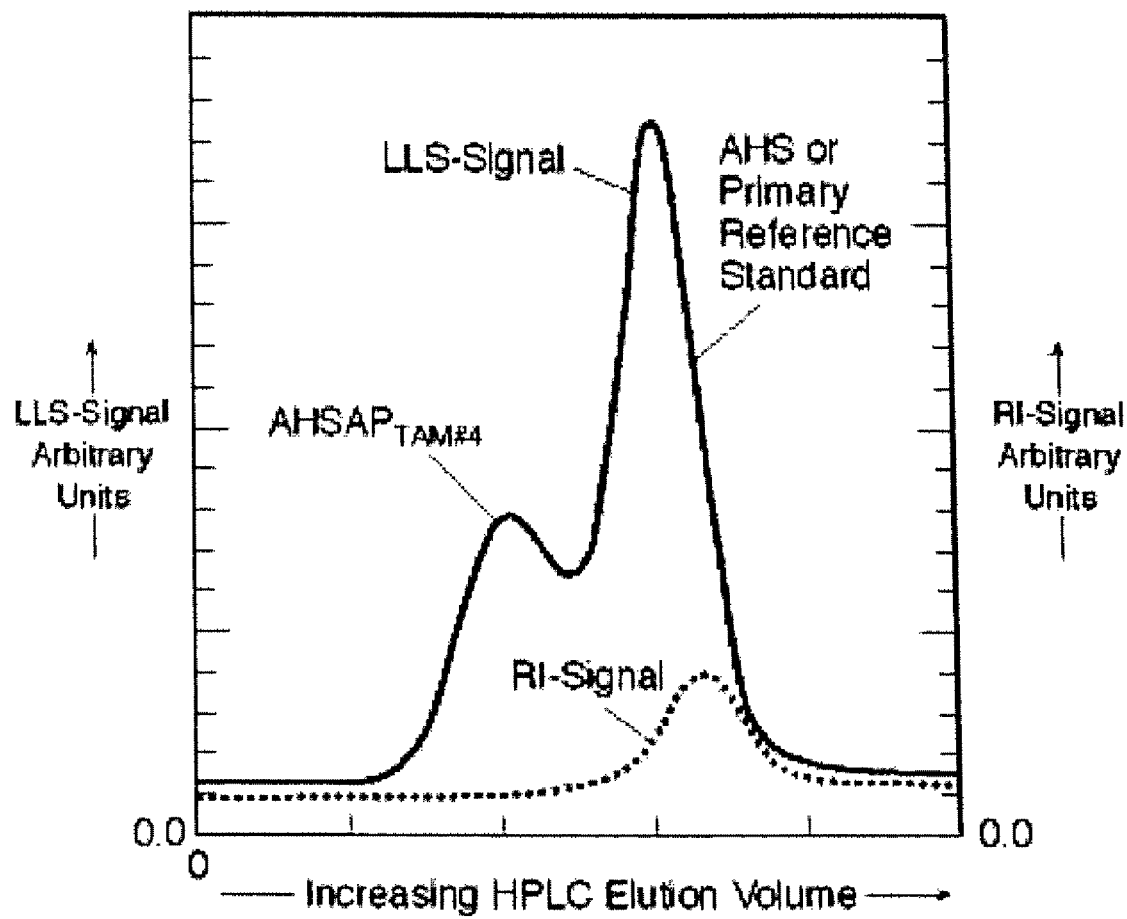

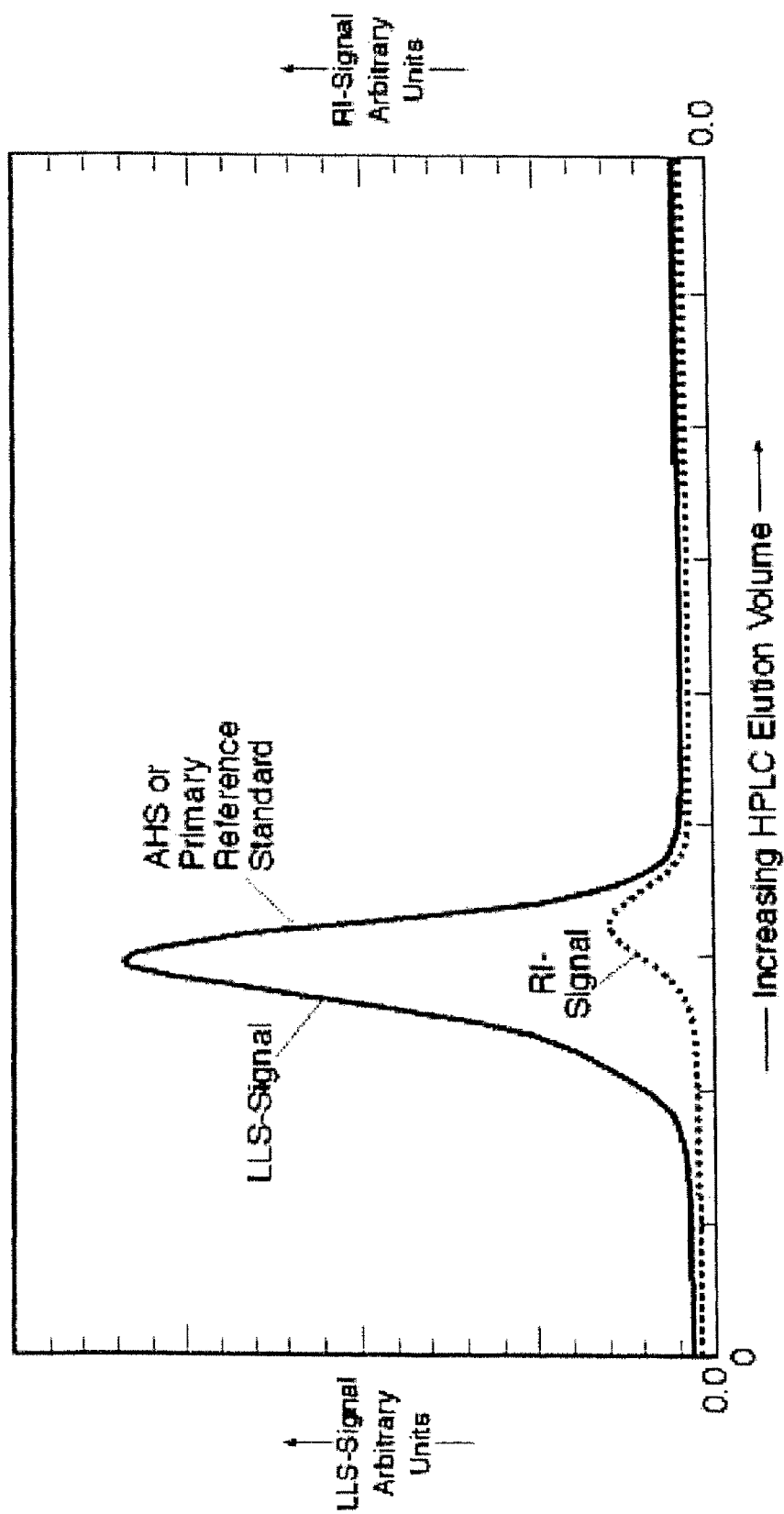

METHOD FOR PRODUCING PURIFIED HEMATINIC IRON-SACCHARADIC COMPLEX AND PRODUCT PRODUCED

CROSS-REFERENCE TO RELATED APPLICATIONS

This application is a continuation of U.S. application Ser. No. 11/176,132 filed on Jul. 7, 2005, now U.S. Pat. No. 7,687,273, issued on Mar. 30, 2010, which is a division of U.S. application Ser. No. 10/600,173 filed on Jun. 20, 2003, now U.S. Pat. No. 6,929,954, issued on Aug. 16, 2005, which is a continuation-in-part of U.S. application Ser. No. 10/371,783 filed on Feb. 21, 2003, now U.S. Pat. No. 6,773,924, issued on Aug. 10, 2004, which is a division of U.S. application Ser. No. 09/999,394 filed on Oct. 31, 2001, now U.S. Pat. No. 6,537,820, issued on Mar. 25, 2003, further claiming the benefit of U.S. Provisional Patent Application No. 60/245,269, filed Nov. 2, 2000, the disclosures of which are hereby incorporated by reference herein.

BACKGROUND OF THE INVENTION

The present invention relates to therapeutically active iron-containing species including parenteral hematinic pharmaceuticals. For purposes of the present invention a "hematinic" means a compound or composition comprising iron in a form that tends to increase the amount of hemoglobin in the blood of a mammal, particularly in a human. While such compounds can be broadly characterized as iron-carbohydrate complexes, which can include dextrans, the present invention is directed to the generic subclass known as iron-saccharidic complexes and includes such species as sodium ferric gluconate complex in sucrose (SFGCS), ferric hydroxide-sucrose complex (FHSC) and/or others characterized as iron saccharates. For purposes of the present invention, such active iron-containing species are referred to generically as iron-saccharidic complexes or active hematinic species (AHS). The term "complex" may have alternate meanings in various contexts in the related art. In one aspect, the term complex may be used to describe the association between two or more ions to form a relatively low molecular weight non-polymeric composition which exists singly under a given set of conditions. This type of complex has been referred to as a "primary complex". An alternate manner in which this term is used is to describe an association or agglomeration of a plurality of primary complexes into a large macromolecule, or "secondary complex." For purposes of the present invention, the latter agglomerates are also referred to herein as macromolecules. For the purposes of the present invention, such macromolecules or secondary complexes are identified as "complexes" and are referred to simply as complexes. As an example of the above distinction, ferrous gluconate is a composition comprising divalent iron ions and gluconate anions. A divalent iron ion and two gluconate anions form a primary complex of relatively low molecular weight (about 450 Daltons) and primary complexes of this type do not become agglomerated into macromolecules when dissolved into an aqueous medium. Ferrous gluconate, therefore, is a not composition which falls within the scope of the term "complex" herein. Ferric gluconate, however, does exist as a complex as that term is used herein because primary complexes of trivalent iron ions and gluconate anions agglomerate to form large macromolecules (and can have molecular weights of from about 100,000 to about 600,000 Daltons, or more). Several embodiments of therapeutically active ferric iron compounds are commercially available, as will be described below. For purposes of the present invention, the term "excipients" means non-hematinically active components, including synthesis reaction by-products and unreacted starting materials, degradation by-products, diluents, etc., present in admixture with therapeutically active iron-containing species such as iron-saccharidic complexes. Such excipients can include one of more sugar, such as sucrose, that may be present in combination with the AHS following synthesis, as an unreacted or partially reacted component, or added to the AHS in the course of preparing a parenteral composition, e.g., commercially available parenteral iron compositions as described below.

Iron deficiency anemia is a blood disorder that can be treated using various therapeutic preparations containing iron. These preparations include simple iron salts such as ferrous sulfate, ferrous gluconate, ferrous fumarate, ferrous orotate and others. Various low molecular weight iron, Fe(III), compounds intended for use as oral or nutritional supplements are known. Such low molecular weight compounds are only useful as oral supplements, since the introduction of materials having high unit concentrations of iron directly into the bloodstream by injection would be contraindicated and could be toxic. In contrast, the compounds of the present invention, intended for parenteral use, have lower iron concentrations and can be used parenterally. For purposes of the present invention, parenteral means introduced into the body by some other means than through the gastrointestinal tract; for example, by intradermal, subcutaneous, intramuscular, intravenous, intramedullary, intra-articular, intrasynovial, intraspinal, intrathecal or intracardiac injection or infusion.

If the use of such orally administered substances fails to ameliorate iron deficiency, the next level of treatment includes parenteral iron administration. Depending on a patient's clinical status, parenteral administration of polyglucan or dextran-linked iron may serve as an effective therapeutic iron-delivery vehicle. Intramuscular injection or intravenous routes may be used to administer these iron dextrans; commercial examples of such products include those having trade names such as "Imferon", and "INFeD". Various clinical conditions that require parenteral iron have shown the practical hematinic value of iron dextrans. The use of iron dextrans is tempered by idiosyncrasies in their synthesis, manufacturing and patient responses such as hypersensitivity. These effects may be exhibited as a severe allergic response evident as anaphylaxis or symptoms as minor as transient itching sensations. Whether such allergic or other adverse effects are due to individual patient sensitivity to the active ingredient or to byproducts, impurities or degradation products in the parenteral solution has not been established.

As an alternative to iron dextrans, iron-saccharidic complexes are regarded herein as non-dextran hematinics. Whereas the iron dextrans comprise polymerized monsaccharidic residues, the iron-saccharidic complexes of the present invention are characterized by the substantial absence of such polymerized monosaccharides. Iron-saccharidic complexes are commercially available, for example, under the tradename Ferrlecit, which is identified as sodium ferric gluconate complex in sucrose (SFGCS). The manufacturer states that the structural formula of the product is considered to be $[NaFe_2O_3(C_6H_{11}O_7)(C_{12}H_{22}O_{11})_5]_n$, where n is about 200, and as having an apparent molecular weight of 350,000±23,000 Daltons. However, it is noted that, based on the published structural formula just recited, the formula weight should be significantly higher, 417,600 (although, as published, the formula is difficult to accurately interpret). Furthermore, the commercial hematinic composition comprises 20% sucrose, wt./vol. (195 mg/mL) in water. The chemical name suggests that therapeutic iron (Fe) in this form is pharmacologically administered as the oxidized ferric form Fe(III) as opposed to the reduced ferrous Fe(II) form. Owing to the charged oxidation state of Fe(III) it has been suggested that gluconic acid (pentahydroxycaproic acid, $C_6H_{12}O_7$) also exists in a coordination complex or ligand form in a sucrose solution. For purposes of the present invention it is to be understood that the chemistry of gluconate, whether held in a ligand complex with Fe(III) or not, does not exempt it from interactions with other carbohydrates that may be present, such as sucrose. Thus, use of the term iron-saccharidic complex will be understood to indicate the existence of a nonspecific and imprecise structure where ionized gluconic acid (gluconate) and sucrose molecules are tenuously associated by various bonding interactions to give a molecular scaffolding that incorporates Fe(III). Another non-dextran hematinic of the present invention is compositionally described as ferric hydroxide-sucrose complex (FHSC). This parenteral hematinic is commercially available under the tradename "Venofer". As with SFGCS, the descriptive name suggests a form of ferric iron, Fe(III), that is present in a spatial complex with sucrose or some derivative of sucrose. Therefore, non-dextran, iron-saccharidic complexes of the present invention include SFGCS, FHSC and mixtures thereof. These iron delivery vehicles include an iron-containing structural complex that, for purposes of the present invention, is designated the active hematinic species (AHS).

For purposes of the present invention, the term AHS is used interchangeably with iron-saccharidic complex, saccharidic iron delivery vehicle, and iron saccharate. The term "saccharate" or "saccharidic" is employed to generically describe iron atom interactions with another individual molecule or its polymers that display a saccharose group structurally identified as

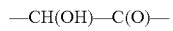

—CH(OH)—C(O)—

The simplest occurrence of the saccharose group is where the two terminal positions in a standard Fischer molecular projection model of a molecule appear as an ald- or a keto-group respectively designated as:

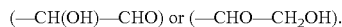

(—CH(OH)—CHO) or (—CHO—CH$_2$OH).

This nomenclature format is also described in Zapsalis, C. and R. A. Beck, 1985, "Food Chemistry and Nutritional Biochemistry," Chapter 6, John Wiley & Sons, pp. 315-321 (incorporated herein by reference to the extent permitted). Such groups and their first oxidation or reduction products occur in molecules recognized as monosaccharides that contain carbon atoms with hydrogen and oxygen in the same ratio as that found in water. By way of example, the aldose sugar known as glucose would have gluconic acid as a first oxidation product and glucitol, also known as sorbitol, as a first reduction product. Both the original monosaccharide represented by the model of glucose and its possible reaction products retain evidence of the characteristic saccharide group in an oxidized or reduced form. While these structural variations exist, both remain recognized as monosaccharides and carbohydrates. In practical nomenclature, the oxidized version of the saccharose group exhibits a carboxyl group which under the appropriate pH conditions will allow it to ionize according to its unique ionization constant and $pK_a$ value. When ionized, the oxidized saccharose group is denoted as a "saccharate" or it can be generically described as a saccharidic acid where the ionizable proton remains with the oxidized saccharose group. If the ionized carboxyl group of the saccharose group is associated with a cation such as sodium, a saccharidic acid salt is formed. For example, oxidation of glucose gives gluconic acid and the sodium salt of this saccharidic acid is sodium gluconate. Similarly, where a ferrous Fe(II) cation is electrostatically associated with the carboxyl group of gluconic acid, ferrous gluconate results. Monosaccharides that are aldoses commonly undergo oxidation to give their saccharidic acid equivalents or, when ionized, monosaccharate forms may interact with selected cations having valence states of +1 to +3. Glyceraldehyde is the simplest structure that demonstrates such an ald-group while dihydroxyacetone serves as a corresponding example of a keto-group. Practical extensions of such structures with six carbon atoms account for the descriptive basis of two carbohydrate classifications, one form being aldoses and the other ketoses. Aldoses and ketoses are respectively represented by monosaccharides such as glucose or fructose. With many possible intra- and intermolecular reaction products originating from monosaccharides, including the glucose oxidation product known as gluconic acid, efforts to complex iron with saccharates can produce an AHS. For purposes of the present invention, AHS is considered to be a more chemically complex embodiment of hematinic iron than suggested by the generic descriptor sodium ferric gluconate complex in sucrose (SFGCS) or ferric hydroxide-sucrose complex (FHSC), and therefore, designations including iron-saccharidic complex or saccharidic-iron delivery vehicle or saccharidic-iron are used interchangeably with AHS. Consequently, intra- and intermolecular reactions or associations from reactions of monosaccharides with iron during hematinic syntheses can coincidentally produce a wide variety of structural species with hematinic properties that are encompassed within the present invention.

Typically iron-dextrans are provided for delivery of up to 100 mg Fe(III)/2.0 milliliter (mL) of injectable fluid, whereas iron-saccharidic complexes can provide 50-120 mg of Fe(III)/5.0 mL volume as commercially prepared in a single dose. As made, many of these iron-saccharidic complex products contain 10-40% weight-to-volume occurrences of non-hematinic excipients as well as synthesis reaction by-products.

While some hematinic agents have an established compendial status under the aegis of the United States Pharmacopoeia (USP) or National Formulary (NF), iron-saccharidic complexes have no acknowledged compendial reference, standardized molecular identity characteristics or documented molecular specificity unique to the active hematinic species. This suggests that the iron-delivery vehicle in non-dextran hematinics such as SFGCS or FHSC has not previously been adequately purified and separated from manufacturing excipients so as to permit detailed characterization. Consequently, there has not been developed a benchmark reference standard or an excipient-free analytical quality control index capable of characterizing one desirable hematinic agent from others having uncertain characteristics. Since the 1975 merger of the USP with the NF to produce the USP-NF compendial guidelines for drugs, standard identities and analytical protocols have been developed for over 3,800 pharmaceuticals while 35% of marketed pharmaceuticals are still not included in the USP-NF. Hematinic pharmaceuticals such as SFGCS and FHSC fall within this latter category. This issue has been recently addressed in "Raising the Bar for Quality Drugs", pp. 26-31, *Chemical and Engineering News*, American Chemical Society, Mar. 19, 2001. As in the case of immune and anaphylactic responses elicited by specific antigens, a fine line of molecular specificity and compositional differentiation can separate a no-adverse-effect level for one hematinic's active molecular structure and excipients from another that may induce such adverse reactions. Thus, there is a need to identify features that document one hematinic's safe and effective characteristics from others where little is known about the iron-delivery vehicle, excipients representing synthesis reagent overage or byproducts of hematinic synthesis reactions. Furthermore, there are no long-term detailed sample archives or data using modern analytical instrumentation that meaningfully characterize the chemical nature of even the safest parenteral iron-saccharidic complexes. Moreover, correlation between variations in normal hematinic manufacturing conditions and their consequential effects identifiable as changes in the chemical structure of a released pharmacological agent have not been identified. The methods of the present invention can address such issues.

The present invention can also provide an analytical basis for a routine protocol in order to fingerprint and characterize iron-saccharidic complexes such as SFGCS, FHSC and others as well as discriminate between competing products and structural transformations exhibited by an individual product.

The need to characterize an AHS is also reflected in the quality control demands of manufacturing processes, particularly where endothermic conditions and heat transfer issues can affect final product quality. Whatever the proprietary synthesis process, possible heat-driven or Strecker reaction byproducts in some commercially released non-dextran products suggest that hematinic product formation is contingent on at least some controlled heat-input during the course of manufacturing. Such excipients would not occur if process temperatures less than about 50° C. were unnecessary. It follows then, that product quality is related, to some extent, to issues of heat transfer rates and duration of heat exposure. Where products are especially sensitive to heat processing conditions, knowledge of excipient profiles can also provide significant insight to the product quality of the active pharmacological substance. In other words, monitoring the safe and effective pharmacological agent can also be indicated by the nature and constancy of excipient occurrence in a drug as released into the marketplace.

Analytical studies on iron-saccharidic complexes, including AHS and its coexisting excipients are hampered by factors of low concentration, molecular interactions, over-lapping analytical signals and so on. For both SFGCS and FHSC, analytical challenges include high concentrations of hydrophilic excipients, including excess reactants and reaction and post-reaction byproducts, from which their respective AHS's have not previously been isolated or reported in terms of their individual properties. Reference standards for pharmaceuticals need to abide by practical protocols that are routinely achievable using methods that are analytically discriminating and able to be verified and validated. There is a continuing need for such methods and application of the present invention can facilitate compliance with such protocols as well as verifying manufacturing consistency and product stability.

SUMMARY OF THE INVENTION

A method for measuring at least one molecular characteristic of an iron-saccharidic complex, the complex comprising at least one active hematinic species (AHS) and one or more excipients, the AHS having a determined value of differential refractive index increment (dn/dc), the method comprising: (A) subjecting the complex to liquid chromatographic analysis (LCA) having a refractive index (RI) detector and in-line eluate stream detection using laser light scattering (LLS); and (B) calculating the molecular characteristics based on the dn/dc value. In a particularly preferred method the dn/dc value is determined by (a) substantially separating the AHS from the one or more excipients to obtain purified AHS; and (b) measuring the dn/dc value of the purified AHS. The method is particularly useful for calculating molecular characteristics such as absolute molecular weight, molecular weight distribution, size, shape, morphology, and dimensional variations.

BRIEF DESCRIPTION OF THE DRAWINGS

FIG. 6 shows LLS and RI data based on HPLC analysis of a sample of iron-saccharidic complex and indicating an iron aggregate peak ($AHSAP_{TAM2}$) by time interval 1 after its manufacture.

FIG. 7 shows LLS and RI data based on HPLC analysis of a sample of iron-saccharidic complex and indicating an iron aggregate peak ($AHSAP_{TAM2}$) by time interval 2 after its manufacture.

FIG. 8 shows LLS and RI data based on HPLC analysis of a sample of iron-saccharidic complex and indicating an iron aggregate peak ($AHSAP_{TAM3}$) by time interval 3 after its manufacture.

FIG. 9 shows LLS and RI data based on HPLC analysis of a sample of iron-saccharidic complex and indicating an iron aggregate peak ($AHSAP_{TAM4}$) by time interval 4 after its manufacture.

FIG. 10 shows the chromatographic signature for an iron-saccharidic complex isolated as Fraction 1, lyophilized, reconstituted and analyzed using RI and LLS-based HPLC.

DETAILED DESCRIPTION

Figure 1:
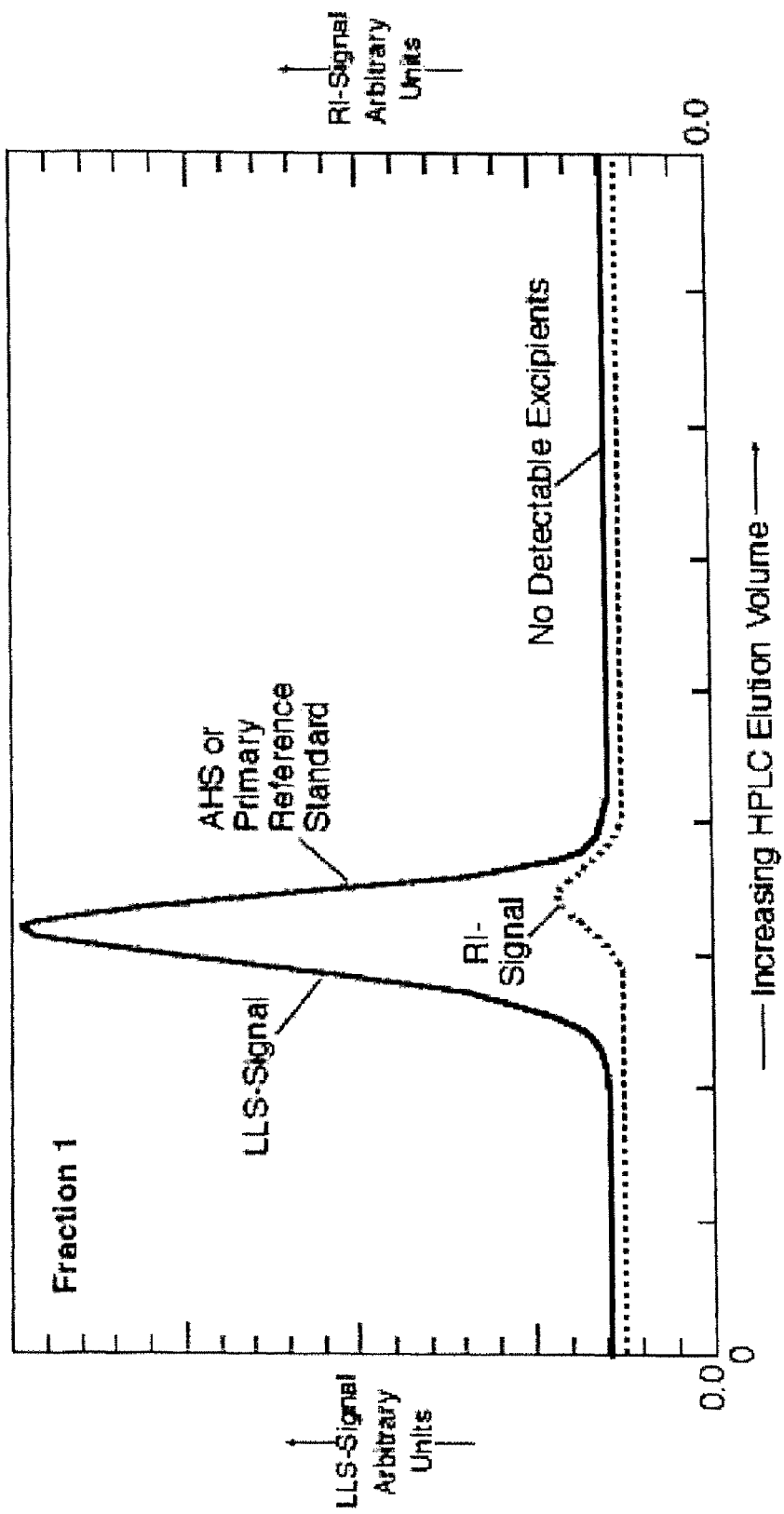
FIG. 1 shows the chromatographic signature obtained for isolated and purified AHS or primary reference standard of an iron-saccharidic complex as isolated in Fraction 1.

Prior to the present disclosure, the AHS responsible for parenteral iron-delivery had not been suitably separated from its excipients with controlled, reproducible purity. Such co-mingling of excipients with the AHS challenged the development of improved hematinic products as well as characterization of the AHS. In view of the improved methods disclosed herein, opportunities are afforded for analytical monitoring of the iron-saccharidic complex to gauge product compliance with manufacturing specifications, to determine storage stability indices and batch-to-batch comparison using a benchmark reference standard. Such a benchmark reference standard has not previously been available, particularly since the AHS had not been isolated. The methods of the present invention allow therapeutically active AHS to be effectively separated and concentrated from coexisting excipients, and then to be dried, or lyophilized, if desired. The present invention provides the information, methods and analytical details for the preparation, characterization and use of sodium ferric gluconate complex in sucrose, SFGCS, ferric hydroxide sucrose complex, FHSC and iron saccharates. The materials are generally referred to as iron-saccharidic complexes or hematinics. It also provides methods for establishing reference standards for these materials that were heretofore nonexistent. The disclosure also provides the analytical basis for routine discrimination in connection with manufacturing and continued monitoring of these products after release. The analytical and other methods disclosed herein are generally applicable to iron-saccharidic complexes including commercial and generic iron-saccharidic complexes as well as current commercial parenteral iron-saccharidic complexes that perform a hematinic function.

Prior to development of the methods disclosed herein, standards for iron-saccharidic complexes were not available because there was no method to separate, purify and characterize the AHS without unduly affecting or destroying the AHS. However, nondestructive characterization of the AHS using high pressure liquid chromatography in combination with laser light scattering combine to provide an analytical method for safely and accurately characterizing such saccharidic-iron complexes. Coupled with the separation and purification process taught herein, there is now a method for providing AHS reference standards with the further opportunity to use such materials in specifying products.

According to the present invention, a method for characterizing the AHS in the absence of its excipients includes separating the AHS and associated excipients into at least two fractions. Since the AHS ordinarily exists at very low concentrations, once separated, it is also preferable to concentrate the AHS in order to permit its detailed analytical study. Although AHS are subject to degradation, they can be concentrated, provided that hydrophilic excipients are substantially absent from the composition prior to or at the time of concentration. Concentration can be effected by drying and, preferably, by lyophilization, but other methods can be employed. After drying, preferably by lyophilization, the AHS is in powder form.

Weak electron bonding interactions such as hydrogen bonding between water and excipients provide challenges in the separation and drying of the AHS. As released, for example in parenteral form, the AHS typically is present in an aqueous system that has a lower water activity ($A_w$) than solute-free water, i.e., pure, water. It is generally accepted that solute-free water has an $A_w$ value approaching or equal to 1.0. Water activity is a parameter corresponding to the availability of the water present in a substance or composition for participating in physical, chemical and biological processes. Water activity is reduced as a consequence of the presence of water soluble or hydrophilic substances, in particular those having a low molecular weight. In other words, a portion of the water present corresponding to the fraction of the water which serves to bond or dissolve the substances is otherwise unavailable. Consequently, water activity diminishes as the number and/or concentration of substances dissolved or bound increases. As most often applied in the food and pharmaceutical industries, elevated water activity values are associated with chemical and biological degradation so that water soluble or hydrophilic substances are added in order to decrease the value of $A_w$. In the present invention, solutes and/or colloids, including materials suspended or dispersed in the aqueous composition, including saccharidic excipients accompanying the AHS, interact with water, e.g., they are hydrophilic or they can hydrogen bond. Such substances reduce the $A_w$ value for water present to a value less than 1.0.

So long as hydrophilic excipients are present in water in which the AHS is present, a portion of the water remains bound to such excipients and removal of water from the composition comprising the AHS, accompanied by its concentration, cannot acceptably be achieved. Consequently, separation of hydrophilic excipients from the AHS increases the $A_w$ value toward 1.0 in the phase or fraction comprising the AHS, and facilitates the concentration, drying and analysis of these preferred species.

Solute effects on water in systems comprising SFGCS and FHSC directly impact upon the drying behavior of these species, including lyophilization, because lowering of their released hydrophilic and excipient concentrations is accompanied by an increased water vapor pressure and an associated increase in the $A_w$. The concept of water activity, expressed as $A_w$, has found its most significant use in the area of food science (see, for example, "Principles of Food Science", edited by O. R. Fennema, "Part II, Physical Principles of Food Preservation", M. Karel, et al., pp. 237-263, Marcel Dekker, Inc. 1975; Encyclopedia of Food Science, edited by M. S. Peterson, et al., "Water Activity in Relation to Food", D. H. Chou, pp. 852-857, Avi Publ. Co., Inc., 1978, each incorporated herein to the extent permitted). The premise is that there is a relationship between the chemical and physical processes that may occur in food storage and the amount and state of water in the foods. The same principles can be applied to other substances or compositions in which water is present and which can be affected by water. Water present in a composition, as a solvent, diluent or otherwise, can be characterized as free or unbound or bound to various degrees to other compounds, for example, in the present case to excipients or the AHS. Various methods can be used to determine the degree to which the water is bound, including determining the amount of unfrozen water in a water containing composition below 0° C., measurement by nuclear magnetic resonance, determination of dielectric properties and measurement of vapor pressure; the latter technique is preferred for its simplicity. In this method, water activity is defined as the ratio of partial pressure of water in the composition or compound in which water is present, to the vapor pressure of pure water at a given temperature. This follows from Raoult's Law where water vapor pressure present in a solution (P) is compared to the vapor pressure of pure water (solute-free,) ($P_o$). As the ratio $P/P_o$ increasingly drops below 1.0, the $A_w$ value becomes smaller, the entropy state for such water decreases, its vapor pressure is lowered, presumably as a consequence of increased water-solute binding interactions, and vapor phase removal of water becomes more difficult. These conditions influence drying processes such as lyophilization. Furthermore, in complex mixtures, in other words, where chemical compounds or complexes may not be completely dissolved or present in the form of a true solution, there can be substantial deviations from the ideal Raoult's Law expression and, furthermore, water activity of the components comprising the composition can differ. It has also been observed in multiphasic compositions that transport or diffusion of water from a component in which Aw is higher to one where it is lower, can occur contrary to what might otherwise be expected based on concentration driving forces (M. Karel et al., page 251). It should also be appreciated that, as a complex composition is dried, the concentration of solutes having differing degrees of interaction with water, for example, different levels of hydrogen bonding, can affect, in a complex and changing way, the ability to remove the water. This is a further important reason to substantially separate or isolate the active hematinic species from their excipients so that appropriate drying process conditions can be determined and controlled. Water can be strongly bound to specific sites on compounds, including the hydroxyl groups of polysaccharides, as well as to carbonyl and amino groups and others on which water can be held by hydrogen bonding, by ion-dipole bonds, or by other strong interactions. Therefore, in the present case, water can be bound to specific sites on the AHS and excipients, for example, as a monolayer. Such water can be present as non-freezable water, unless temperatures are significantly below 0° C.; additionally, it can be present as non-solvent water. In the present compositions, water is known to bind strongly to sucrose so that $A_w$ in a sucrose-containing composition is depressed. Therefore, drying, particularly freeze drying (described in detail below), can be adversely affected.

Whether lyophilized (freeze-dried) or not, the ability to prepare purified AHS as a discrete substance provides significant capabilities for defining the chemical and structural features that characterize such hematinic products. With verifiable and reproducible parameters established for such a hematinic, it is possible to establish a quality control framework of, for example, batch-to-batch uniformity of the AHS. Departures from validated structural uniformity in the AHS can be used as an index of storage stability and to assist in identifying cause-effect relationships of variables in manufacturing processes. The ability to isolate and analytically characterize these agents using modern technology, particularly laser light scattering, helps to define the attributes of such iron-saccharidic complexes.

Little is known about the synthesis of iron-saccharidic complexes for hematinic use because such syntheses have generally relied on proprietary methods. Similarly, there is little analytical information available for such complexes. The active pharmacological hematinic species or iron-delivery vehicle in the hematinic is believed to be less than five percent according to weight-by-volume measurements of total solids and it may be as low as 1.0 percent. Thus, in commercial products, measurement of the characteristics of the AHS as released has typically been carried out in the presence of a high percentage of hydrophilic excipients. Such low concentrations of the unique ferric iron-delivery vehicle accompanied by relatively large amounts of excipients challenged characterization of the AHS. Furthermore, no reference standard had been established for AHS since it was believed to be so unstable that it could not be isolated for analysis. With the effective separation of AHS from its excipients based on the methods described herein, these methods can be extended so as to develop improved hematinic agents alone or admixed with other pharmacological agents. For example, purified AHS can be combined with erythropoietin or other useful drugs.

Access to excipient-free AHS permits closer analytical monitoring of the AHS and its pharmaceutical performance. Moreover, for pharmaceuticals where excipients account for a high percentage of the total solids weight, the ability to independently monitor such excipients is similarly significant for issues such as quality control, manufacturing and clinical performance. Unanticipated clinical effects can be a consequence of previously unnoticed or changed distributions and types of excipients that occur during manufacturing. For food systems, the development of byproduct compounds due to thermal effects on saccharides provides important insights into the adequacy and control of process manufacturing steps. Such issues have been addressed for other products by H.-J. Kim, U.S. Pat. No. 5,254,474 while others have focused on thermally generated aldehydes in biotechnology applications, see C. M. Smales, D. S. Pepper, and D. C. James, 2000, "Mechanisms of protein modification during model antiviral heat-treatment bioprocessing of beta-lactoglobulin variant A in the presence of sucrose," *Biotechnol. Appl. Biochem.*, October, 32 (Pt. 2) 109-119. Detection of compounds linked to thermal effects on saccharides in pharmaceutical manufacturing can also be significant where heat is a factor in synthesis. Indeed, identification of nominal excipient levels and distributions in complexes such as FHSC and SFGCS can verify that proper synthesis conditions have been employed.

The present invention provides methods for separating hematinics including SFGCS, FHSC and iron saccharates into at least two distinct fractions. Furthermore, the methods are generally applicable to products in which iron is supplied as an iron-saccharidic complex or an iron delivery vehicle where iron is held in association with negatively charged carboxyl groups derived from carbohydrates. Initially, one fraction of the hematinic, identified herein as Fraction 1, comprises the iron-saccharidic complex or iron-delivery active hematinic species, AHS. Another fraction, identified herein as Fraction 2, comprises a mixture of substantially all of the excipients that coexist with the AHS in the original composition, e.g., as synthesized or as released. Excipients in Fraction 2 can be, for example, hydrophilic organic or ionic compounds.

The solutes or suspended or dispersed components present in liquid Fractions 1 or 2 can be used for detailed analytical study or characterization purposes, and can be further concentrated or used as starting materials in the development of new products. The present invention discloses the separate, but related, analytical roles that these fractions can play so as to facilitate the establishment of benchmark reference standards that characterize sodium ferric gluconate complex in sucrose, SFGCS, and ferric hydroxide sucrose complex, FHSC, from their excipients. Furthermore, the present invention discloses methods for preparing concentrated, lyophilized and optionally reconstituted AHS. Separation of the various components is achieved starting with the as-synthesized or commercially available hematinic with its combined AHS and excipients in an aqueous (water) composition and then selectively relocating or extracting the excipients so that they are present in a substantially separate aqueous phase. After establishing these two fractions, each can undergo detailed analytical characterization, further purification if desired, and concentration to satisfy analytical, synthesis or manufacturing goals.

Hematinics are a class of pharmaceuticals designed to convey hematopoietically useful iron and Fraction 1 comprises from at least about 75 to about less than about 100%; preferably; from at least about 80 wt. % to about 99.9 wt %; more preferably from at least about 90 wt. % to about 99.9 wt. %; most preferably from at least about 95 wt. % to about 99.9 wt. %; of the AHS intended for parenteral delivery, whereas Fraction 2 comprises correspondingly low levels of the AHS, for example, less than about 0.1 wt. % and substantially all of the excipients originally present in the hematinic composition.

1. Substantially Separating the AHS from Coexisting Excipients.

At least one active hematinic species, AHS, can be isolated or substantially separated from excipients present in an as-synthesized hematinic or in commercially available pharmaceuticals characterized as iron-saccharidic complexes. Such separation has been achieved by the inventors herein as a consequence of their determining several significant characteristics of hematinic compositions which comprise an iron-saccharidic complex, including: (1) that it is necessary to increase the $A_w$ value of the AHS-containing phase or fraction; (2) AHS display at least one detectable iron species with a formula weight of from about 250,000 to about 3,000,000

Daltons or more; (3) manufacturing and stability variations can result in more than one detectable iron-containing species being present; (4) Fe(III)-containing species can display different shapes, e.g., as measured by laser light scattering; (5) Fe(III)-containing AHS have an electrical charge; and (6) Fe(III)-containing AHS can have a detectable oxidation-reduction (redox) potential indicative of the presence of ferric iron, (Fe(III), or ferrous iron (Fe(II). Separation of AHS from its excipients into at least two fractions may be achieved by using one or more of the following methods, with or without preliminary pH stabilization in the range of about 6.0 to about 8.0; preferably about 6.4 to about 7.8, more preferably about 6.6 to about 7.6 for example about 6.8 to about 7.4:

1. Electrokinetic migration where AHS concentration depends on direct electrical current flow that causes electrically charged AHS to deposit on a charged collection surface or within an aqueous volume in which a charged surface is present separate from its excipients.

2. Electrokinetic-based membrane technology wherein a cathode and an anode are placed in a water system separated by a semipermeable membrane partition. A direct current applied over the membrane causes the electrically charged AHS to concentrate on the appropriate electrode due to attraction between opposing charges. Such AHS concentration on a single electrode in one compartment allows the dialysis-mediated removal of hydrophilic excipient carbohydrates through the semipermeable membrane into the accompanying compartment. Preferred semipermeable membranes include cellulose, cellulose acetate, cellulose ester or regenerated cellulose. In order to maintain retention of the AHS in one compartment the membrane has a preferred molecular weight exclusion size of about 90,000 to about 300,000; preferably about 150,000 to about 200,000. Preferred conditions for the method include the use of distilled, deionized water at a pH of about 7.5 to about 9.8; a pressure of about 1.0 atm; and a temperature of about 2° C. to about 50° C. The rate of dialysis removal of hydrophilic excipients can be improved by frequent changes in aqueous dialyzing fluid. The process is generally described by Ficks Law, $F=-DA(dc/dx)$, where F=the total flux; D is the diffusivity of the species in the medium, e.g., water; A is the surface area available for diffusion and $dc/dx$ is the concentration gradient of the excipients through the membrane.

3. Capillary electrophoresis technology that concentrates AHS from coexisting excipients. Capillary electrophoresis, sometimes referred to as capillary zone electrophoresis, relies on the introduction of an electrically charged analyte within a fused silica capillary with size dimensions of about 50 to about 75 microns in diameter by about 50 to about 100 cm in length to which is applied a voltage of up to about 30 kilovolts. The differential electrokinetic migrations of charged substances in the composition can be detected and recorded by a variety of methods described herein, including UV-VIS, fluorescence and mass spectroscopy. The final migration positions of the electrically charged substances in the capillary can be documented as an electropherogram. This method can be particularly useful owing to the substantial electrical charge on the AHS within iron-saccharidic complexes.

4. Column chromatography, which is a particularly preferred process for selective separation of AHS. Owing to the discrete formula weight, size dimensions, shape and charge of the AHS in contrast to coexisting excipients, AHS engage in different stationary phase interactions as a liquid carrier or eluent (e.g., water) transports them over and/or through a solid support. Thus, differential diffusion or migration rates responsible for such separations reflect relative electrical charge and/or size exclusion differences that retard or accelerate elution of these substances through the chromatography system. Separations can also be adjusted by modifying the porosity, electrical charge or adsorption properties on the surface of the stationary phase. Such chromatographic processes may be carried out at from about 3° C. to about 150° C.; preferably from about 15° C. to about 35° C.; typically, 25° C. using aqueous or non-aqueous solvents supplied to columns in a singular or multiple serial flow scheme. Chromatographic partitioning of AHS may be carried out at any pressure drop over the inflow and outflow of a column. The internal pressure of the column may range from below atmospheric pressure to any pressure that the column and stationary phase material can tolerate. Operational pressures above about one atmosphere (0.1 MPa) are preferred, but pressures up to about 10,000 pounds per square inch (69 MPa) may be employed. Eluants supplied to the column can include any solvent or diluent so long as AHS is maintained as an iron-saccharidic complex. Such eluants include $C_1$-$C_6$ alkanols, ethanolamine, dimethylsulfoxide, carbonyl-based solvents, dimethylforamide, water, aqueous buffer solutions and various admixtures including water-saccharide solutions. The use of from about 2.0 to about 25 weight percent of a primary alcohol may be useful for controlling potential microbial growth. Suitable stationary phase materials are commercially available including porous silica, crosslinked polyglucans identified as dextrans, crosslinked methacrylate polymers, copolymers of ethylene glycol and methacrylate, crosslinked polystyrene, alumina, agarose gels, cyclodextrins and cationic as well as anionic exchange packings may be used. Particularly preferred stationary phases for column chromatographic separation of AHS from its excipients in a hematinic composition is crosslinked polyglucan or dextran available commercially in various grades as Sephadex G-10, G-15 and G-25 (Amersham-Pharmacia Biotech., Piscataway, N.J.); and, a commercial column identified as $GMPW_{XL}$ having a 13 micron particle diameter with pore sizes of from about 100 to about 2000 Angstroms and a polymethylmethacrylate backbone (Tosoh Biosep, Montgomeryville, Pa.). When employing solid stationary phase packing, pore diameter in the range of from about 30 to about 9000 Angstroms is preferred; more preferably from about 100 to about 8000 Angstroms. The dextran stationary phases are particularly preferred for the bulk separation of AHS, e.g., using low pressure chromatography; and polymethylmethacrylate backbone is particularly preferred for analytical characterization of the AHS, e.g., using HPLC.

The methods of the present invention can be used singularly or in combination with each other in order to separate AHS that is primarily or substantially responsible for the desired pharmacological action attributed to FHSC or SFGCS. The substantially separated and, consequently, purified AHS serves as the basis for establishing a primary reference standard. In turn, the primary reference standard can then provide a standard for use in monitoring manufacturing and pharmaceutical quality control. If desired, the AHS can be subjected to further purification using the methods taught herein. For example, where analysis of a hematinic composition using HPLC in combination with, for example, LLS and RI, shows the presence of a shoulder on, or a peak preceding the AHS primary reference standard, a further separation method can be employed. As described herein, such a shoulder or secondary peak may be present in a hematinic composition as a consequence of departure from preferred manufacturing conditions or as a result of storage of the hematinic composition, particularly in the presence of hydrophilic excipients. The further separation or purification process comprises additionally separating the first to elute material from the preparative chromatographic column using the HPLC analytical results or data obtained directly from an LLS detector in combination with the preparative chromatographic column. In this manner, a significant percentage or substantially all of the undesirable aggregated AHS can be separated from the preferred AHS. Where an initial non-AHS peak is present and distinctly separate from the characteristic AHS primary reference standard peak, substantially all of the aggregated material corresponding to such a peak can be separated from the desired AHS, for example, in Fraction 1. Where a shoulder appears on the primary reference standard AHS peak, as will be further discussed below, separation of substantially all of the undesirable, e.g., aggregated material, may necessarily carry with it some of the preferred AHS or, conversely, not all of the aggregated material may be removed. The extent of separation and purification can be determined with reference to the data generated according to the methods of the present invention. Therefore, in addition to removal of substantially all of the lower molecular weight, primarily hydrophilic excipients present in the hematinic compositions of the present invention, the methods taught herein can result in an AHS that is substantially purified as well with regard to aggregated iron complexes.

Applying the teachings of the present invention, a discrete active hematinic species (AHS) can be separated from excipients supplied in commercially available parenteral compositions characterized as iron-saccharidic complexes; the separated material can serve as a "primary reference standard." One method of separating the AHS from coexisting excipients employs low pressure gel permeation chromatography (GPC). In the present invention, low pressure refers to operation of the chromatography column at about ambient pressure, including at a pressure slightly above ambient as a consequence of pumping fluid to a packed column to which are attached valved lines and, optionally, other equipment, including one or more analytical instruments or detectors. This technique can be used not only for analysis of the separated materials, but also for producing bulk quantities of AHS for preparation of new parenteral compositions. Preferably, the column packing comprises epichlorohydrin-crosslinked polyglucans with demonstrated molecular weight or size exclusion characteristics greater than about 5,000 Daltons; more preferably with size exclusion characteristics greater than about 1,500 Daltons are preferred. Suitable equipment is available from Amersham-Pharmacia Biotech, Piscataway, N.J. Furthermore, ion-exchange gels with GPC properties and affinity chromatography columns are also suitable.

The separated AHS of the present invention, substantially free of excipients, generally has a high absolute molecular weight when measured by the techniques described herein, e.g., HPLC in combination with LLS and RI. Such high absolute molecular weights are typically greater than about 25,000 Daltons and can be greater than about 30,000, 50,000, 75,000 or 100,000 to about 3,000,000 Daltons or more; for example, molecular weights of about 200,000 to about 2,500,000; about 250,000 to about 1,000,000; or about 275,000 to about 850,000. These high molecular weights are to be contrasted with the low molecular weights reported in the literature for compounds intended for use in tablet form. Such low molecular weight compounds are less than about 2200 Daltons, more typically less than about 1700 Daltons and, in the present invention, are separated from high molecular weight AHS when using, e.g., column packing having exclusion characteristics of greater than about 5000 Daltons. Consequently, as described herein, separation of high molecular weight AHS from low molecular weight excipients distinguishes the AHS of the present invention on the basis of molecular weights, even where such low molecular weights are as high as 5000 Daltons.

The AHS is typically present in Fraction 1 and the excipients elute thereafter in Fraction 2. Since material elutes from the column in a continuous fashion, the reference to fractions is based on that portion of material eluted from the column in which there is present substantially all of the preferred or primary reference AHS that has been substantially separated from its excipients. One method for marking such a separation of eluted material is to observe where the LLS signal closely approaches or returns to the baseline value for the mobile phase following the appearance of the initial peak or peaks indicating the presence of AHS and/or aggregated AHS (as further discussed below). In a preferred method, a solvent reservoir supplies an aqueous-based diluent or solvent by gravity or metered flow to a chromatography column of any selected diameter or length provided that the length is at least twice the diameter. The column can be constructed of glass, stainless steel, polycarbonate or another material that is non-reactive with the composition and diluents or solvents employed and able to contain a stationary chromatographic support material, also referred to as a bed. The bed typically comprises beads having suitable porosity but other forms of the bed may be manufactured in situ within the confines of the column, such as a poured-in-place porous polymer. In carrying out the process of the present invention, initially an aqueous-based solvent (or diluent), referred to as the mobile phase, is passed over as well as through the interstices of a beaded, porous support bed. As the liquid stream or eluate exits the column, it is conducted, e.g., through tubing, to one or more detectors that analyze the stream in order to determine its baseline properties. Detectors may be positioned to deal with a series flow of eluate from one detector to the next or a split stream flow that allows parallel, multiple detector monitoring. Such detectors target eluate characteristics in terms of real time volumetric flow of the stream. Suitable detectors are employed to measure and record such stream properties as pH, electrical conductivity, electrochemical reduction potential, refractive index (RI) and other useful analytical properties. UV-VIS absorption (A) and refractive index (RI) are preferred detectors for measuring the baseline properties of the mobile phase.

Injection of an iron-saccharidic complex, for example a commercially available parenteral composition, into the aqueous stream leading into the top of the packed column bed ensures that various constituents in the composition will be distributed over and through the porous chromatographic beads. Without wishing to be bound by theory, it is believed that separation of the different sized chemical species comprising the iron-saccharidic complex proceeds, for example, by a sieving effect and, potentially, with hydrogen bonding interactions. Chemical species larger than the pores are excluded from the pores and they first exit the column in a relatively small eluate volume ($V_{e1}$). As the flow of the sample continues through the column, progressively smaller molecules can become entrained within the pores and subsequently exit the column in a relatively larger eluate volume ($V_{e2}$). Thus, large species such as AHS within the hematinic elute first ($V_{e1}$) in Fraction 1 and smaller excipient chemical species elute later ($V_{e2}$) in Fraction 2. Such a chromatographic separation produces at least two components or fractions, the AHS and its excipients, when applied to the initial parenteral volume of hematinics including components such as SFGCS, FHSC. As will be described later, larger sized byproduct or degradation species can also elute with or prior to the AHS. The AHS separation is substantially complete so that it is separated from original coexisting excipients, particularly hydrophilic excipients, and including those excipients that may have distinctive fluorescent properties. Consequently, the AHS is produced in a high $A_w$ aqueous fraction, Fraction 1, that is substantially free of excipients and substantially all of the excipients are present in a second fraction, Fraction 2, characterized by a low $A_w$ condition. Acid hydrogen-base binding (AH-B) dynamics within the column bed can further increase the effective elution volume ($V_{e2}$) for excipients from the column in addition to their size interactions with the chromatographic bed. Acid hydrogen-base binding interactions are generally discussed by Hodge, J. E. and E. M. Osman, 1976, Chapter 3, in "Food Chemistry," O. R. Fennema Ed., Marcel Dekkar, New York, pp. 92-96; and Zapsalis C. and R. A. Beck, 1985, "Food Chemistry and Nutritional Biochemistry," Chapter 10, John Wiley & Sons, pp. 588-591 (each incorporated by reference to the extent permitted). For purposes of the present invention the term "substantially free" when used in reference to the separated AHS being substantially free of excipients means that the fraction containing the AHS includes from greater than 80 wt. %; generally greater than about 85 wt. %; preferably greater than about 95 wt. %; more preferably greater than about 98 wt. %; still more preferably greater than about 99 wt. % and most preferably greater than about 99.9 wt. % up to less than or equal to about 100 wt. % of the AHS eluted from the column (in other words, there can be present trace amounts of excipients and the amount of eluted AHS may not include a minor or trace amount of AHS that may be retained in the column, tubing, detectors, or lost during processing). Correspondingly, such excipients as are originally present in the composition fed to the chromatographic column, or possibly generated during processing, are contained in the subsequent, excipient fraction, Fraction 2, and is equal in amount to the above stated values subtracted from a value of 100 wt. %. For example, if the AHS fraction comprises greater than about 99.9 wt. % AHS, excipients can be present in an amount less than about 0.1 wt. %. Separation of AHS from non-hematinic components, excipients, also typically separates the AHS from sucrose that may have been added during the synthesis process or, possibly, post-synthesis. To the extent that sucrose can be readily separated from the AHS, it is to be understood that the AHS of the present invention is distinct therefrom, although a chemical formula or structural diagram may suggest that sucrose is present. Consequently, with regard to the two commercially available hematinics, the separated AHS in one instance corresponds to sodium ferric gluconate complex and, in the other, to ferric hydroxide-sucrose complex, although the commercial products may be identified as being "in sucrose." Since sucrose is readily separated from AHS by the methods taught herein, for the purposes of the present invention, sucrose is an excipient. However, if desired, sucrose can be added to a composition that includes the AHS of the present invention if its presence is considered to serve a useful function, e.g., to modify the characteristics of a parenteral composition.

The presence of the AHS, compared to the excipients, in the chromatographic eluate stream can be observed using laser light scattering, as described. Additionally, the elution profile of the AHS and excipients can be detected by using one or more different types of detectors whose output signals are simultaneously recorded for the eluate stream. In a preferred method, one detector is employed that is sensitive to wavelength ($\lambda$) using a UV-VIS absorbance detector and another is a concentration sensitive refractive index (RI) detector. The dual, independent output signals from these detectors are processed and separately recorded as two independent ordinate axes (y-axes) against a common abscissa (x-axis) expressed in units of cumulative eluate volume (e.g., milliliters) or slices (i) as discussed earlier. This method can identify where so-called Fraction 1, comprising substantially all of the AHS effectively ends and Fraction 2, comprising substantially all of the excipients, effectively begins. Experimental evidence demonstrates that the fractions are sufficiently separated in time so that the AHS can be obtained substantially free of excipients.

According to the Beer-Lambert Law, light absorbance is related to the concentration of a specific light-absorbing species. The absorbance (A) of a light absorbing species is expressed as:

$$A = \epsilon b c \quad \text{Equation 5}$$

where c is the concentration of a light absorbing species in moles per liter (M/L); b is the light path in centimeters (cm) through the light absorbing species; and, $\epsilon$ is a proportionality constant known as the molar extinction coefficient. This proportionality constant is unique to a light-absorbing species at a given wavelength of light. This fundamental law accounts for the fact that light absorbance for a light absorbing species at a specific wavelength ($\lambda$) converts into a quantitative measure of its molar concentration. Hence, positive increases in absorbance at a prescribed wavelength for an analyte corresponds to increases in its molar concentration. For monitoring the AHS of SFGCS or FHSC in a chromatographic eluant stream, 435 nm is preferred because of high extinction coefficient for that wavelength, i.e. 6.590 $\log_{10}$, for iron-saccharidic complexes.

For the preparation of substantially excipient-free AHS using chromatographic separation, the $A_{430\ nm}$ value is tabulated against column eluate volume. This can be transformed into a chromatographic elution profile where $A_{430\ nm}$ ordinate (y-axis) values and eluate volumes (x-axis) are plotted against each other. As discussed, the larger AHS elutes from the chromatographic column before smaller excipients. So long as a change in absorbance ($\Delta A$) with respect to changes in eluate volume ($\Delta V$) or $\Delta A/\Delta V$ consistently shows a positive ratio ($+\Delta A/\Delta V$) above a solute-free baseline eluent signal, AHS concentration increases in eluate volume concentration. For a negative ratio ($-\Delta A/\Delta V$) the opposite is true. Where the $\Delta A/\Delta V$ ratio makes a transition from (+) to (−) the chromatographic elution of the AHS is maximized as a "chromatographic peak." From this point onward, as the chromatographic profile continues to display a negative ratio ($-\Delta A/\Delta V$) the AHS concentration diminishes in the eluate volume. This is true for AHS concentrations so long as the $A_{430\ nm}$ continues to asymptotically decrease and approach an $A_{430\ nm}$ value of about 0.0. As this measurement signals an end to the elution of the AHS, the concentration sensitive RI detector begins to respond to increasing amounts of hydrophilic and other excipients included in the eluate. As above, a positive (+) change in the ratio of RI with respect to changes in volume ($+\Delta RI/\Delta V$), signals increasing concentration of excipients. At the eluate collection volume where $\Delta A/\Delta V$ still displays a negative ratio ($-\Delta A/\Delta V$) asymptotically approaching a value of about 0.0 A and RI-detector begins to signal a $+\Delta RI/\Delta V$ slope, this marks the effective boundary where Fraction 1 substantially ends and Fraction 2 effectively begins. Fraction 1 comprises the AHS in a high $A_w$ environment and Fraction 2 comprises the hydrophilic and other excipients in low $A_w$ environment. In this manner, an elution profile is determined.

The eluate boundaries that define the separation where Fraction 1 substantially ends and Fraction 2 effectively begins can alternatively be determined by measuring the percent spectral transmission of the AHS in column eluate at 430 nm. A suitable instrument for this purpose is a "ColorQuest XE" system manufactured by Hunter Associates Laboratory, Inc., Reston, Va. Increases in the light transmission of the eluate as the AHS present in the eluate asymptotically approaches zero percent, can indicate substantial separation or an end to elution of the AHS. A subsequent increase in RI-response of the eluate stream marks the beginning of the eluate volume comprising excipients. In a further alternative embodiment, a demarcation between where Fraction 1 substantially ends and Fraction 2 effectively begins can be determined by measuring the $A_{620\ nm}$ anthrone-based absorbance of the eluate stream. Since both the AHS and the excipients have notable dextrose equivalent (DE) absorbency, the detectable $A_{620\ nm}$ DE-value will be minimal between Fraction 1 and Fraction 2. The principles that underscore this analytical concept have been described by R. Dreywood, "Qualitative Test for Carbohydrate Material," *Indus. and Eng. Chem., Anal. Ed.*, 18:499 (1946); J. E. Hodge and B. T. Hofreiter, "Determination of Reducing Sugars and Carbohydrates," *Methods Carbohydrate Chem.*, 1:384-394 (1962); and more recently by C. Zapsalis and R. A. Beck, "Food Chemistry and Nutritional Biochemistry," Chapter 6, John Wiley & Sons, pp. 353-354 (1985) (each of the disclosures of which are incorporated herein to the extent permitted).

The methods of the present invention allow for preparation of large production batches (for example, from greater than about 500 milligrams to greater than or equal to about 1.0 gram; or from about 1.0 gram to about 10 grams or more; from about 1.0 gram to about 100 grams or more; from about 1.0 gram to about 1 kg or more; for example, if desired, hundreds or even thousands of kilograms can be produced by the present method) or small analytical samples (from about 5.0 to about 500.0 milligrams) of the AHS present in iron-saccharidic complexes of any type can be prepared. Since the AHS is the preferred component of complexed iron present of these parenteral compositions, the ability to separate the AHS forms the basis for the primary reference standard. Separation of Fraction 1 permits further detailed chemical and/or structural analyses; such methods are described elsewhere herein. However isolated, the AHS, e.g. Fraction 1, as well as the excipients, e.g., Fraction 2, may be further concentrated for detailed study.

The present invention is also suitable for production of small scale amounts of AHS (from less than about 1.0 mg to less than about 5.0 mg), preferably by way of high pressure (or high performance) liquid chromatography (HPLC). An appropriate chromatographic solid support can be used to separate the AHS from its excipients. This results in AHS transfer into a hydrodynamic volume within the column that displays a high $A_w$, e.g., approaching a value of 1.0. The excipients are transferred into a low $A_w$ hydrodynamic volume having a low $A_w$, e.g., less than the value of the AHS-containing phase. The operational principle for this method is similar to that of the low pressure chromatographic method described above, but the stationary column bed materials for the HPLC method are more finely divided so as to withstand pressures of from about 5,000 to about 10,000 pounds per square inch (about 35 to about 69 M Pa). This results in slower flow rates of eluate from the column, but it is more than compensated for by the high hydrostatic pressure. A silica-based stationary bed that depends on adsorptive-desorptive analyte separation phenomena can be used to produce a separation of the AHS from its excipients. Such silica-based separation performances however are difficult to control and require accurate preparation of an azide-containing aqueous mobile phase; consequently, they are subject to greater analytical errors. Furthermore, shedding of particulates from silica-based beds complicates or can preclude effective use of a LLS detector. Thus, a polymeric HPLC column, such as a $GMPW_{XL}$ brand manufactured by Tosoh Biosep, Montgomeryville, Pa., that employs an aqueous mobile phase is preferred over silica-based columns. Such HPLC analysis of, for example, a commercially released form of iron-saccharidic complex requires preliminary 0.02 micron filtration through, for example, an Anotop 25 brand inorganic membrane (Whatman, Maidstone, UK).

2. Methods for Characterizing the AHS Primary Reference Standard and Coexisting Excipients.

Analysis for iron reveals that more than about 90% of the iron intended for hematinic purposes resides in the high $A_w$ fraction designated as Fraction 1 above, generally from at least about 75 wt. % to less than about 150 weight %; preferably from about 80 wt. % to about 99.9 wt. %; for example, from about 90 wt. % to about 99.9 wt. %; from about 95 wt. % to about 99 wt. %; and excipients reside in the low $A_w$ fraction designated as Fraction 2. Iron atoms in Fraction 1 can be quantified by atomic absorption spectroscopy (AAS) but iron quantification by AAS alone is not determinative of hematinic functionality of the products of the present invention.

The relevant characteristic of a non-dextran hematinic of the present invention is based on its ability to deliver a physiologically tolerable or benign source of ferric iron, Fe(III), preferably via parenteral means. This ferric iron composition is a parenterally acceptable species that resembles properties of an association colloid. An association colloid is a reversible chemical combination due to weak chemical bonding forces wherein up to hundreds of molecules or ions aggregate to form colloidal structures with sizes of from about 1 to about 2000 nanometers or larger. Such colloids of ferric ions interacting with saccharidic compounds exhibit directional migration in an electric field in addition to optical activity identified by laser light scattering (LLS). LLS properties relevant herein relate to the Tyndall effect where an incident light beam ($I_o$) passing through a colloid emerges from it at a 90° angle to its original path. Light scattering only occurs if the light interacts with macromolecules such as starches, proteins or other colloidal species where the wavelength of incident light approaches size dimensions of the molecules. Light scattering can occur as destructive interference where the scattered wavelengths interact to cancel each other out or by constructive interference where two wavelengths of light reinforce each other. Mathematical evaluation of LLS data permits size and shape evaluations of various colloidal species. Size, for example, may be estimated in terms of molecular weight for a single molecule or the formula weight for a multi-molecular or ionic aggregate. The weight expressions in either case represent the sum of atomic weights of all atoms present in such structures. The structural diversity of most aggregates or molecules such as polymers is such that they exist as a frequency distribution of varying weights, typically expressed as an average or mean molecular weight distribution (MWD). Apart from size, colloidal shape can have important implications. For example, if its shape is that of a thin rod, a random coiled structure or a sphere its interaction with other molecules or structures can vary. LLS, including multi-angle laser light scattering (MALLS) or low angle laser light scattering (LALLS), combined with one or more methods of HPLC-integrated detector analysis can be used for evaluating iron-saccharidic complexes. For purposes of the present invention, reference to LLS should be understood to include MALLS, the latter being a preferred type of detector. The use of LLS measurements herein provides a superior and preferred analytical method for characterizing an iron-saccharidic complex that is normal, in other words, represents the preferred AHS resulting from suitably controlled synthesis, or one that displays evidence of decay or degradation products. The fundamental mathematical relationships and operation of HPLC in combination with laser light scattering and refractive index detectors for the characterization of macromolecular structures and association colloids has been reported. (see P. Wyatt, Light scattering and absolute characterization of macromolecules, *Analytica Chimica Acta*. (1993) 272:1-40; incorporated by reference to the extent permitted). As discussed herein, such techniques are applicable to iron-saccharidic complexes comprising AHS.

Acquisition of LLS data is particularly useful for identifying AHS in saccharidic-iron complexes, particularly where a benchmark analytical reference standard is required. LLS data can be obtained from an individual batch based on an isolated sample or LLS data can be obtained using in-line analysis of an eluate stream from a continuous process containing the AHS following its liquid chromatographic isolation. In other words, once a saccharidically bound ferric iron complex has been produced and examined by LLS alone or in combination with other methods such as those disclosed herein, batch-to-batch comparisons of manufacturing continuity can be routinely verified in terms of formula weight as well as morphology of the pharmacological species. Characterization of AHS size and shape features can be used to monitor AHS manufacturing processes, AHS product quality and AHS stability by using LLS algorithms that are integral with the operational software of LLS enhanced HPLC. Specifically, as taught herein, size and dimensional attributes for so-called normal AHS (e.g., primary reference standard material or the preferred AHS) and so-called abnormal AHS (e.g., degraded or aggregated AHS) structures are determined from a standard Debye plot generated by operating software such as ASTRA (Wyatt Technology Corp., Santa Barbara, Calif.). The details of such an application described in P. Wyatt, Light scattering and absolute characterization of macromolecules. *Analytica Chimica Acta*, 272:1-40 (1993), incorporated herein by reference to the extent permitted. Preferred AHS has been observed to have a generally spherical shape and to be about 10 nanometers or smaller in size, whereas degraded or aggregated AHS, such as material that elutes from a chromatographic column before the preferred AHS, tends to be greater than about 10 nanometers in size, for example from about 10 to about 30 nanometers or more, for example, from about 20 to about 30 nanometers or more. Size and shape dimensions can be relevant factors for physiological and metabolic tolerances as well as for their tissue disposition of a hematinic. Thus, the application of LLS methods is preferred for routine characterization (including after manufacturing and during storage) and manufacturing monitoring for the hematinics of the present invention.

Laser light scattering of AHS provides characterization parameters in terms of absolute formula weight or absolute molecular weight. However, since the AHS is not a monomolecular species, but instead behaves as an association colloid, the use of absolute molecular weight is particularly preferred. Such LLS-based molecular weight measurements are preferred over other methods of weight estimation that provide a so-called relative molecular weight. Relative molecular weight measurements of the AHS do not rely on the size and shape dependent physical interactions of light with an AHS as a basis for estimating its weight. Instead, relative molecular weight measurements rely on standard methods of size exclusion chromatography (SEC), also sometimes referred to as gel permeation chromatography (GPC). Both SEC and GPC are hereinafter used interchangeably. In GPC analysis, the effective size of a macromolecule or aggregate such as an AHS, not its formula weight, determines its elution volume and exit from a calibrated chromatography column. Hence, the relative elution and transit of the AHS through a GPC column relative to a series of calibration standards in a narrow band above and below the expected weight of the AHS provides the basis for assigning a relative formula weight to the iron-containing complex. Using this concept, a concentration sensitive detector such as a refractive index (RI) detector would be used for detection of the AHS and its calibration standards as they elute from a column. As a concentration sensitive detector, RI-measurements rely on the changes in the indices of light refraction (n) as analyte (for example, solute) concentrations (c) increase or decrease in their respective flow through the RI-detector cell. At evenly spaced time intervals, ratios of such changes in refraction and concentration are recorded as $dn/dc$ values. Each $dn/dc$ value is unique to a specific analyte or solute and the $dn/dc$ value characteristic of one substance is not an a priori value universally applicable to any other specific substance. Such $dn/dc$ values recorded for the elution of known calibration standards and unknown analytes can be acquired and recorded at precise time intervals. Each $dn/dc$ measurement in the overall elution profile of a liquid chromatography column is referred to as a slice (i). The slice number, its elution time or elution volume can be used to reference this slice. Elution time of a slice multiplied by the flow rate of the eluent to the column gives the elution volume. Records of slice numbers in terms of volume or number do not compromise the general significance of this data-recording concept. Thus, a plot of $dn/dc$ (ordinate) versus slice numbers (abscissa) over the course of a GPC measurement gives an elution profile for calibrating standards with respect to any unknown substances that may be totally unrelated to each other, yet they have $do/dc$-detectable masses suitable for instrumental monitoring.

Because standard GPC procedures do not recognize significant physical interactions common to all large molecular or colloidal structures, GPC weight evaluations for the AHS present in SFGCS, FHSC or other similar hematinics, can be susceptible to analytical errors. Furthermore, RI-based GPC methods are unable to characterize the shape and topological features of the AHS including, for example, structural branching. Also, estimations of relative formula weight using RI-dependent GPC methods are also subject to data variations, are sensitive to minor analyst errors and completely insensitive to dimensional variations of species within association colloids that have a high density. For association colloids, and FHSC and SFGCS in particular, these features are important because nonsaccharidically aggregated iron atoms can coexist along with the desired iron-saccharidic complex containing the AHS. Thus, it is important to recognize that RI-based GPC can provide relative formula weight values for analytes of AHS with reasonable accuracy and reasonable precision, but the method overlooks other important characteristics of AHS structure.

Based on well-known principles of light scattering physics, isotropic particles with small dimensions such as macromolecules and colloids, interact with light so as to permit the calculation of their absolute weight and shape. This is true for the AHS contained in FHSC and SFGCS. Unlike GPC-RI based analysis, the absolute formula weight for a colloidal species can be determined independent of any calibration curve that depends on pre-established graded molecular weight standards (M. J. Vold and R. D. Vold, 1964, "Colloid Chemistry," Reinhold, N.Y.; and Zapsalis, C. and R. A. Beck, 1985, "Food Chemistry and Nutritional Biochemistry," Chapter 8, John Wiley & Sons, pp. 507-547 hereinafter, Zapsalis and Beck, 1985) (each incorporated by reference to the extent permitted). It is established that the intensity of light scattered ($I_\theta$) by a particle through an angle of $\theta$ depends on the intensity of the incident light beam ($I_o$), the light path distance ($\gamma_s$) through the light scattering volume and the polarizability ($\alpha$) of the particle. For unpolarized light the equation is $$R_\theta(1+\cos 2\theta) = I_\theta \gamma_s^2/I_o = 8\pi^4/(1+\cos 2\theta) \quad \text{Equation (1)}$$

The term $R_{74}$ (1+cos 2θ) is the basis for the Rayleigh ratio. Extension of this light scattering measurement to very dilute solutions of particles with sizes smaller than the wavelength of incident light ($I_o$) gives the expression $$R_\theta = 2\pi^2 \eta_o^2 [(\eta-\eta_o)/C]^2/L\lambda^4 \cdot CM = K^*CM \quad \text{Equation (2)}$$

where $R_\theta$ becomes the Rayleigh ratio (R); $\eta$ is the refractive index of a solution containing particulate species, $\eta_o$ is the refractive index of a solvent without particulate species; C is the concentration of solute in terms of mass per unit volume; M is the molecular or formula weight respectively for a molecule or particulate species; L is Avagadro's number; $\lambda$ is the wavelength of light; and $K^* = 2\pi^2 \eta_o^2 [(\eta-\eta_o)/C]^2/L\lambda^4$ is the optical constant. This expression provides a basis for establishing the Rayleigh ratio (R) or that fraction of incident light ($I_o$) scattered by a particle when a wavelength ($\lambda$) of incident light is comparable to or larger than the size of some particulate species. Accordingly, R is related to formula weight of an analyte such as the AHS in SFGCS, FHSC and other iron-saccharidic complexes by the physics of light scattering phenomena and not relative comparisons to GPC calibration curves based on unrelated materials. Independent of instrument detector geometry for detecting the Rayleigh ratio (R) when incident light ($I_o$) interacts with particulates, a relationship stands where $$R = K^*CM \quad \text{Equation (3)}$$

Consistent with in-stream eluate measurement concepts detailed above, where do/dc values are acquired for GPC-RI based systems, Rayleigh ratio (R) measurements are acquired for each slice in other words "i", $R_i$, and the Raleigh ratio is simply the product of each slice's concentration ($C_i$), molecular weight ($M_i$) and the optical constant ($K^*$) or, $$R_i = K^* C_i M_i \quad \text{Equation (4)}$$

Light scattering also allows for characterization of structural consistency of the AHS in iron-saccharidic complexes based on dissymmetry ratios between light scattered at some forward angle θ and that light scattered at its supplementary angle 180-θ ($I_\theta/I_{180-\theta}$). Of all possible light scattering angles, about 45° and 135° serve as instructive reference points. When a plot of $I_\theta/I_{180-\theta}$ (ordinate) versus L/λ (abscissa) is constructed, the structural dissymmetries for spheres, rods and random coils are readily determined by way of reference to Zapsalis and Beck, 1985, p. 535.

If the AHS is substantially isolated, such as Fraction 1 discussed above, it may be harvested in (a) bulk production amounts or (b) small analytical amounts typical of that found in liquid chromatographic eluate streams. In either case, LLS methods offer a preferred analytical method for establishing a routine reference standard for any iron-saccharidic complex in this pharmaceutical class.

The ability to produce purified AHS or iron-saccharidic complex using teachings of this disclosure allows it to be comprehensively analyzed and characterized, including defining its colloidal and molecular attributes. Suitable analytical and characterization methods applicable to the AHS, and to SFGCS and FHSC in particular, include ultraviolet (UV) spectrophotometry, visible (VIS) spectrophotometry and combined UV-VIS spectrophotometry, including photo-diode array (PDA) methods, infrared (IR) spectroscopy, electron spin resonance (ESR), pulse polarography, energy dispersive X-ray analysis (EDS), circular dichroism (CD) and optical rotatory dispersion (ORD), fluorescent spectroscopy, polarimetry, pyrolysis, and pyrolysis mass spectroscopic analyses, nuclear magnetic resonance spectroscopy, differential scanning calorimetry (DSC), liquid chromatography integrated with mass spectroscopy (LC-GC), matrix assisted laser desorption/ionization mass spectrometry (MALDI-MS) techniques, analysis utilizing radioactive isotopes including radioactive iron, antibodies to hematinic substances, capillary electrophoresis and inductively-coupled plasma spectrometry, atomic absorption analysis, electrochemical analysis, as well as specific pH storage and stability studies and targeted glucosidic-degradation of the AHS with saccharidic product analysis. In MALDI-MS, laser light is used to ionize a macromolecular analyte and desorb its ions from a sample matrix into a vacuum system. The method is used to measure the mass of a wide variety of macromolecules in conjunction with mass spectrometry.

Furthermore, the ability to separate the AHS into at least two fractions, Fraction 1 (high $A_w$ fraction), and Fraction 2 (low $A_w$ fraction), also permits independent analysis of excipients that are concentrated in Fraction 2. Discriminative excipient fingerprints can be used to characterize the AHS as well as contribute to product identification and monitoring quality control and assurance. The occurrence and verification of typical or expected excipients supports standardization and monitoring of manufacturing. This improves the likelihood for favorable patient use in clinical settings where the hematinic is administered. Since excipients can account for over 75 percent of the total solids in typical commercial parenteral compositions, excipient verification and analysis can be an important matter. Moreover, since thermally treated saccharides are known to produce identifiable chemical markers that reflect their processing history, these as well as surplus reactants and byproducts developed during hematinic manufacturing (for purposes of the present invention, all such materials are generally included in the term "excipients") can be used to monitor and characterize both the hematinics and processes used to produce them.

There are at least three possible manifestations wherein ferric ions interact or exist in hematinic iron-saccharidic complexes. Firstly, the preferred principal agent, namely the AHS, behaves as an association colloid and it is the desired iron-saccharidic delivery vehicle. Secondly, high formula weight aggregates can develop from the AHS and they may also be detected. Thirdly, iron can exist as a complex with surplus saccharidic reactants and/or byproducts of synthesis reaction steps. This form of iron can be found with hydrophilic excipients in Fraction 2. It is particularly preferred that parenteral compositions be monitored, as well as Fraction (2), for (a) iron content, (b) residual amounts of saccharidic reagents, and (c) evidence of thermally-dependent synthesis reaction byproducts. A particularly preferred method for monitoring such analytes includes the use of liquid chromatographic analysis with refractive index (RI) and in-line eluate stream detection using at least one of the following: laser light scattering (LLS), electrochemical detection (ECD), photodiode array (PDA) based UV-VIS spectrophotometry, infrared (IR) spectroscopy, and liquid chromatography coupled with mass spectrometry (LC-MS), and, optionally, one or more of the analytical and characterization methods described above. Whereas RI is a concentration sensitive detector that allows quantification of excipient saccharides, ECD detectors respond to metal and nonmetal-containing compounds having characteristic electrochemical oxidation-reduction potentials and UV-VIS based PDA analysis permits detection of thermally produced saccharidic derivatives in addition to low formula weight iron-complexed species.

Figure 2:
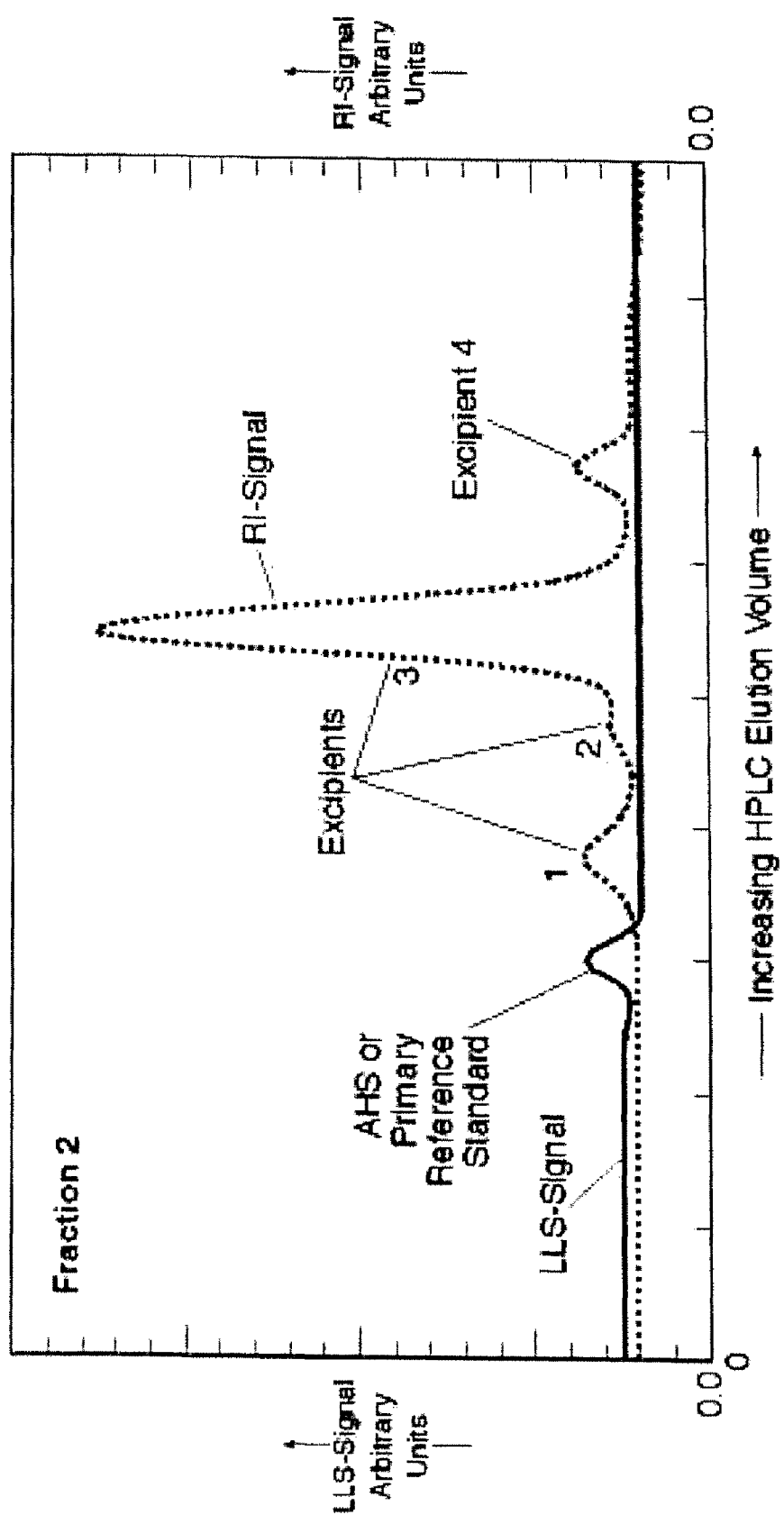
FIG. 2 shows the chromatographic signature obtained for four isolated excipients in Fraction 2, including added trace amount of AHS or primary reference standard.
Figure 3:
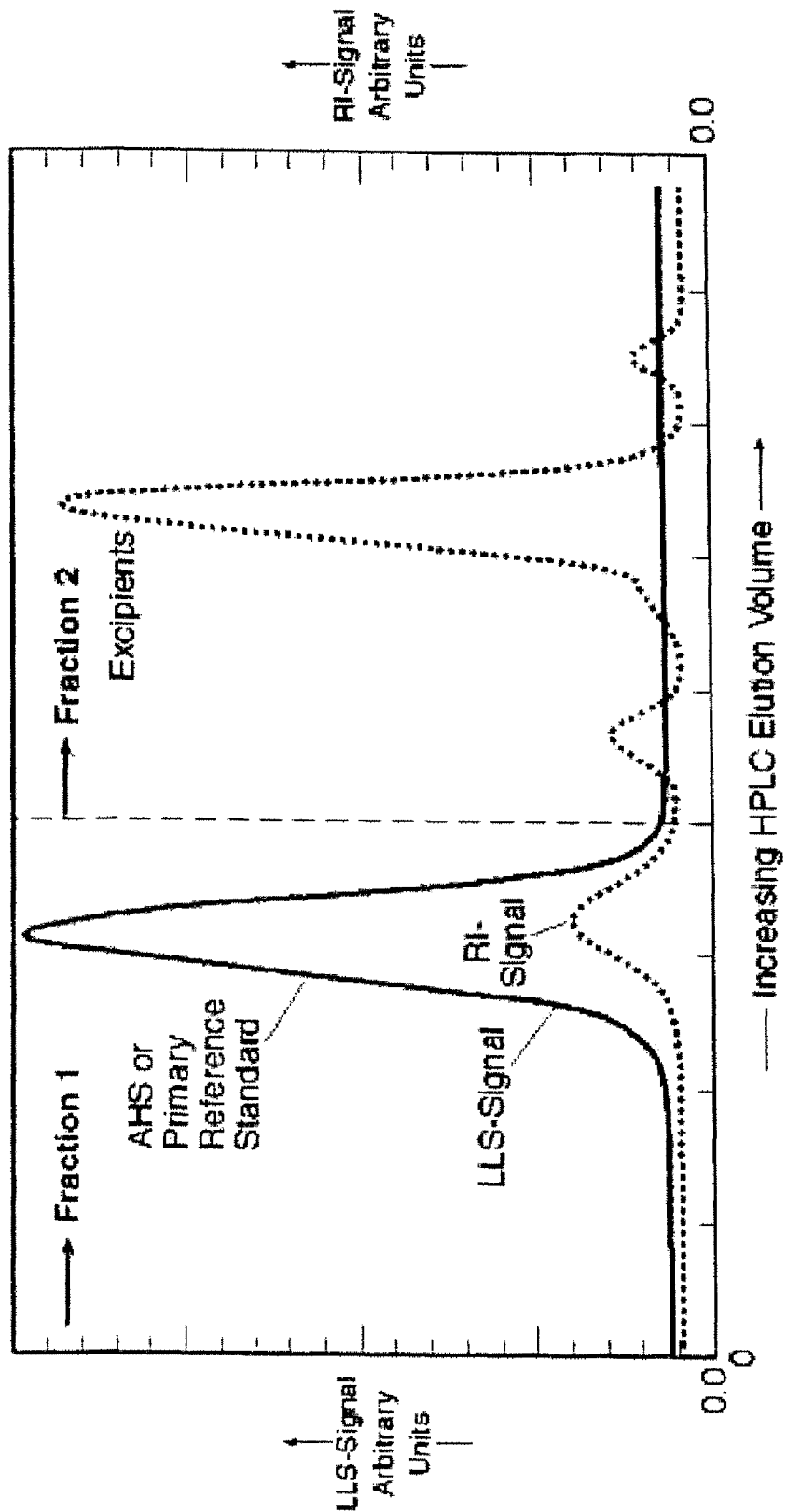
FIG. 3 shows refractive index (RI) and laser light scattering (LLS) analytical results for a sample of iron-saccharidic complex partitioned into Fraction 1 (AHS) and Fraction 2 (excipients) using high pressure liquid chromatography (HPLC).

The methods of the present invention further include methods for characterizing the AHS and its coexisting excipients. Application of HPLC to a previously prepared sample of Fraction 1 comprising AHS using the polymeric column described above, in combination with in-stream dual RI and LLS detectors of the HPLC eluate provides the results illustrated in FIG. 1. This figure shows the separated and purified chromatographic signature for the AHS present in Fraction 1 and, furthermore, that it is free of excipients. Such an HPLC elution signature is a preferred result for a manufactured hematinic comprising an AHS, for example a product released in a sealed glass ampoule. FIG. 2 illustrates the chromatographic signature for four excipients present in Fraction 2 obtained from the same sample that provided Fraction 1. In this test, a small amount of the AHS from Fraction 1 was intentionally introduced into Fraction 2 so that relative positions of the excipients to the AHS could be observed. It is worth noting in FIGS. 2 and 3 that excipients are better monitored by an RI detector because RI is a concentration sensitive property whereas an LLS detector is mass sensitive and responds better to AHS than to excipient carbohydrates. These effects are clearly shown in FIG. 2 where only a trace amount of pure AHS was added as an internal benchmark for relative measurement of excipient elution progress. RI in this case fails to sense any occurrence of purified AHS yet the LLS signal records its presence as an analytical species. FIG. 3 further illustrates that the LLS and RI-based HPLC method using a polymeric column can be used to analytically separate the AHS from its excipients. That is, the AHS component is separated into a high $A_w$ hydrodynamic volume, while at the same time the coexisting excipients that originally accompanied the AHS are substantially separated into hydrodynamic column volumes that elute after elution of the AHS. These results are consistent with those in FIG. 1 for the primary reference standard previously isolated as a discrete entity whereas FIG. 3 represents results for a multicomponent initial composition (AHS and excipients). This confirms that the methods of the present invention can be used to monitor hematinic compositions such as those produced commercially that comprise AHS and excipients.

Figure 4:
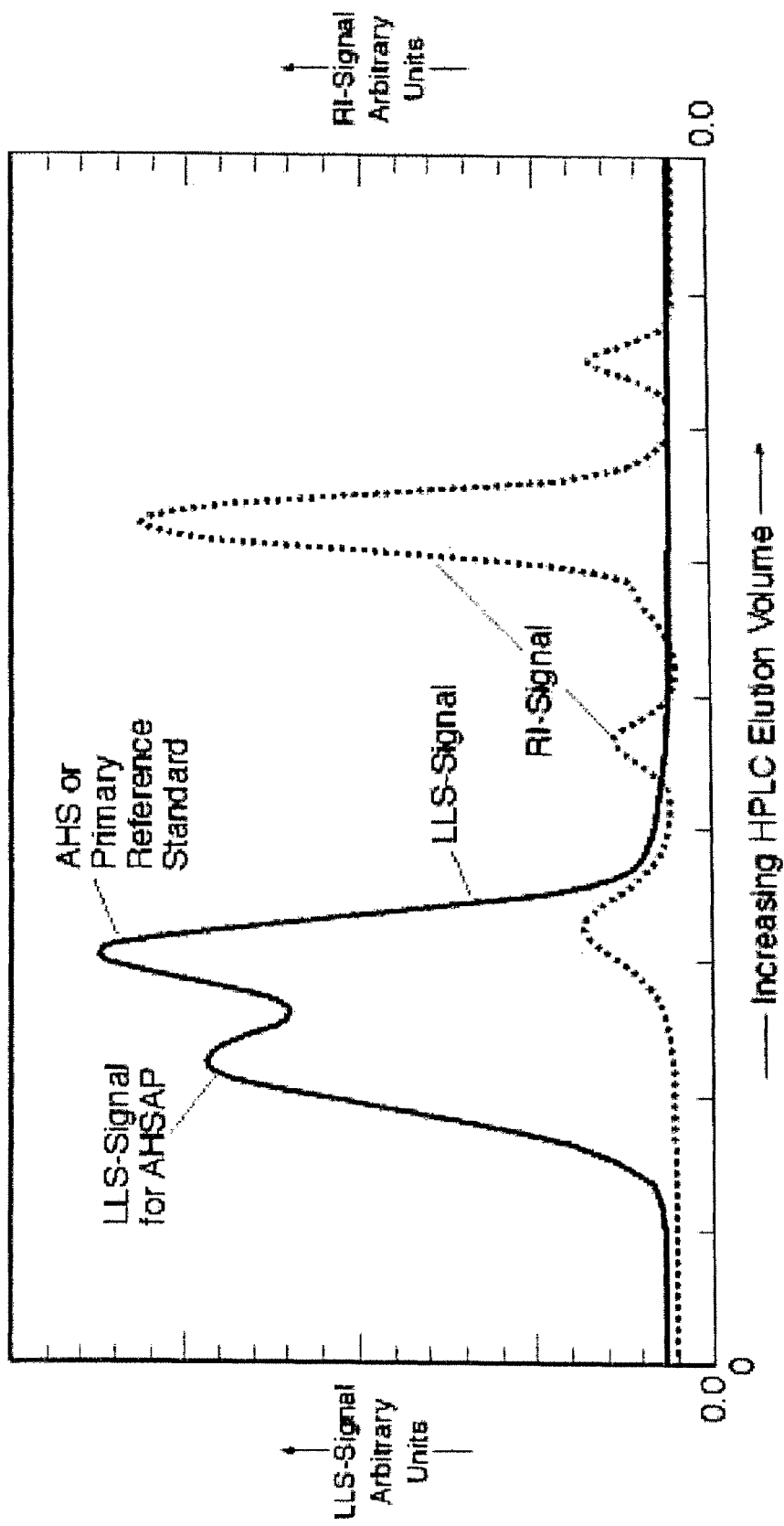
FIG. 4 shows LLS and RI data based on HPLC analysis of a commercial sample of iron-saccharidic complex and indicating structural deviations from AHS or primary reference standard indicated as active hematinic species aggregate peak (AHSAP)
Figure 5:
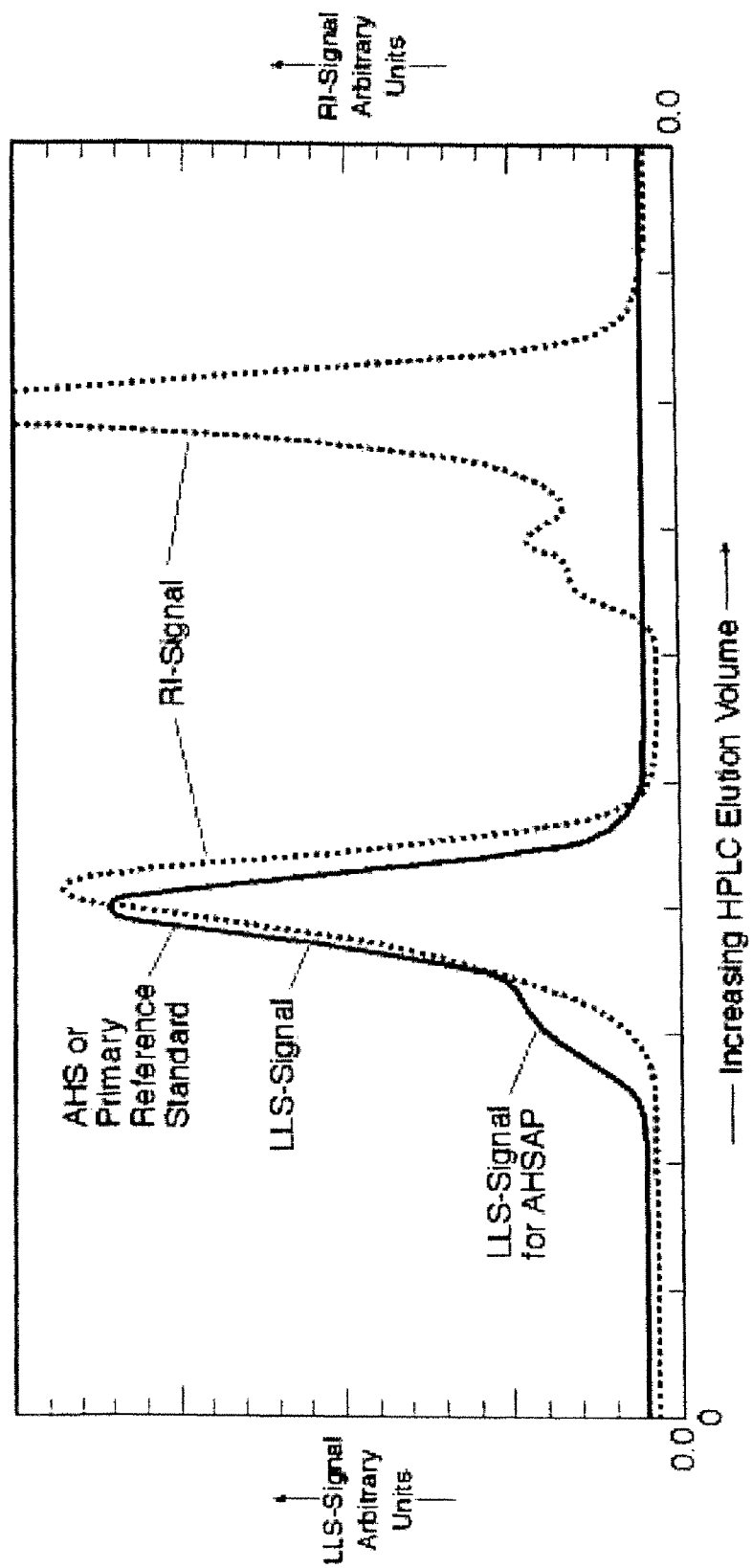
FIG. 5 shows LLS and RI based on HPLC analysis of a second commercial sample of iron-saccharidic complex and indicating structural deviations from AHS or primary reference standard indicated as active hematinic species aggregate peak (AHSAP)

Conditions such as instability and aging of the AHS and manufacturing variability can be monitored in iron-saccharidic complexes using HPLC analysis equipped with at least LLS as one detector mode. Furthermore, LLS-based HPLC used in conjunction with a concentration sensitive detector, such as RI, can be used to monitor structural variations in the nominal chromatographic peak signature for an AHS. Such variations can be seen in the chromatograph in FIG. 4, particularly when compared to that produced by the primary reference standard in FIG. 1 or the separated mixture in FIG. 3. Similarly, FIG. 5 shows the presence of an altered AHS peak in another manufacturer's hematinic product. It is noted that different detectors can provide different information, for example, the LLS-chromatographic detector and the concentration sensitive RI-detector. The concentration sensitive RI-detector senses and records analyte concentration but not its mass, which is independently documented by the LLS-detector. Thus, the LLS-based detector can sense increasing mass of a species formed as a consequence of, e.g., complexing or cross-linking of AHS, that elutes before the AHS primary reference standard. Since the AHS, as illustrated in FIG. 1, is the desired hematinic substance, the species shown in FIGS. 4 and 5, represent even higher formula weight byproducts that are believed to arise from the AHS. The new peak appears to develop at the quantitative expense of the preferred AHS.

The methods of the present invention can be used to monitor storage stability of hematinics comprising an AHS. Like most organic molecules, AHS is subject to structural instability, such that it can degrade or transform, even within sealed glass delivery ampoules used for hematinics, to give new species. Such structural transformations of an AHS are time dependent and may also be promoted by temperature. Evidence of structural AHS transformation over time is evident for a series of LLS and RI-based HPLC profiles for iron-saccharidic complexes stored in sealed glass delivery ampoules at room temperature in the dark for 6, 12, 22 and 25 months after manufacture. The pertinent chromatographic profiles for these products correspond, respectively, to FIGS. 6, 7, 8 and 9. Evidence of structural change is apparent when comparing the unsymmetrical AHS peaks in these figures against the preferred and symmetrical primary reference standard peak exhibited by the AHS in FIG. 1. The new entity indicative of AHS degradation, and detected by LLS, elutes from the column before the primary reference standard or AHS, which also can be seen in the figures. The new entity has features of a very dense, high formula weight structure, conceptually similar to "BB shot". These characteristics are determined based on the Debye plot generated by processing the light scattering data using the ASTRA-brand software incorporated in the LLS equipment, referred to earlier (Wyatt Technology Corp., Santa Barbara Calif.), and the methods and calculations described in the 1993 *Analytica Chimica Acta* journal reference, also referred to above. Debye plots permit the acquisition of specific LLS data which, in conjunction with root mean square (rms) or radius of gyration ($R_g$) measurements, permit size determinations of molecular species or colloids. For FIGS. 6-9, the rms-value indicating particle diameter sizes gives an average value equal to or greater than 20 nm. The corresponding rms-value for the chromatographic signature of AHS in FIG. 1 is less than or equal to 10 nm; well below the practical detection limit of LLS. Thus, the methods of the present invention can be used for monitoring the quality and storage stability of a hematinic composition comprising AHS.

Commercially produced hematinics can be monitored for the AHS, as well as for excipients, during the manufacturing process, at the conclusion of manufacturing, e.g., at the time of packaging, and after manufacture, e.g., if the product is stored. Similarly, an iron-saccharidic complex composition comprising the AHS after separation of the excipients, such composition in the form of an aqueous composition or after drying, e.g., by freeze drying, can also be monitored in the same manner. The iron-saccharidic complex comprising the AHS can be monitored not only during manufacturing, but also as it is stored from shortly after manufacture, such as from about one week thereafter, as well as after a moderately short storage period of about 6 months to for as long as about five years or more after manufacture; extended storage can be from about 1 year to about five years; or from about 1 year to about 3 years. In each instance, the AHS can be monitored by comparison of its properties, including various analytical properties as discussed above, e.g., the chromatographic signature obtained using HPLC in combination with LLS and RI to a primary reference standard.

As described above, the smaller LLS-detectable peak resulting from degradation or modification of the AHS originally present is an extremely high formula weight substance, identified in FIGS. 6-9 as an AHS aggregate peak (AHSAP). The substance responsible for this characteristic AHSAP has a formula weight in the range of from about 350,000 to about 3,000,000 Daltons or more based on light scattering, but ultracentrifugation and other methods can also be used to establish the high formula weight of this species. It is believed that the AHSAP is unrelated to excipients normally occurring as a consequence of the AHS synthesis or manufacturing process. The AHSAP appears, instead, to be related to an aging phenomenon, but it may also result from significant departures from preferred manufacturing conditions. The methods of the present invention can be used to identify the levels of quantitative tolerance of the AHSAP in a parenteral hematinic product. The occurrence and detection of an AHSAP at any time after manufacture ($AHSAP_{TAM}$) of an iron-saccharidic complex can be compared to the total quantitative HPLC signal for the AHSAP detected after a prescribed storage period of the hematinic while exposed to defined conditions ($AHSAP_{TOTAL}$). By way of example, the storage period could cover any convenient period of time, for example from about 6 months to about 10 years or longer; alternatively from about 1 to about 8 years; or from about 1 to about 5.0 years. If, for example a 5 year period is used, at 5 years the $AHSAP_{5yrTOTAL}$ would provide the basis for establishing the maximum acceptable decomposition or modification of the measured characteristics of the hematinic after its release. In other words, by the time 5 years had elapsed the AHS may have decayed into pharmacologically useless iron aggregate and compositional residues distinctly unlike the intended embodiment of the initially released iron-saccharidic complex for parenteral use. Thus, the $AHSAP_{TAM}$ quantified at any time up to $AHSAP_{5yrTOTAL}$, expressed as an occurrence ratio, $[AHSAP_{TAM}]/[AHSAP_{5yrTOTAL}]$, can provide a time-dependent stability ratio or index for gauging hematinic quality and actual percent composition of intact AHS remaining in a hematinic product. There is currently no such standardized way to quantitatively address aging and decay of iron-saccharidic complexes once they are released into commerce. It should be appreciated that the occurrence ratio is not limited to use of the 5 year elapsed time interval, but, rather, as noted above, it applies to any convenient elapsed time interval selected. It can be useful to gauge iron-saccharidic complex aging and stability against defined conditions where, for example, 50 percent of the iron-saccharidic complex remains in its original form at the time of manufacture or release into the marketplace, as compared to iron other than iron-saccharidic complex; for example free or unbound iron or iron aggregate, thereby allowing determination of an iron-saccharidic complex half-life. As the $[AHSAP_{TAM}]$/AHSAP$_{TOTAL}]$ ratio approaches a value of about 0.5, this 0.5 ratio-value can serve as a pharmacokinetic index and guardrail to ensure that the manufactured product will have at least 50% of its iron-saccharidic complex still intact, as intended for initial release. Although the basis for quantitatively gauging the shelf life of hematinics here cites a value of 50% survival for iron-complexation in an AHS, practical quality standards higher than 50% are more desirable; as a practical matter, from about 0.5 to about 0.98; preferably from about 0.75 to about 0.95; more preferably from about 0.80 to about 0.99; for example, any single value between about 0.5 and less than or equal to about 1.0 (and correspondingly, for iron other than iron-saccharidic complex, AHS, values of from 0.02 to less than about 0.5; from about 0.05 to about 0.25; and from about 0.01 to about 0.20; for example, any single value from equal to or greater than about 0 to less than or equal to about 0.5) may be established by a standards setting organization or by the manufacturer. Such an established ratio of $[AHSAP_{TAM}]/AHSAP_{TOTAL}]$ is particularly useful for purposes of indexing, warranting or standardizing the clinical efficacy, performance and safety of such hematinics. Prior to the present invention, there was no basis for assigning quality compliance standards to iron-saccharidic complexes using standards that are generally applicable to drugs. As described herein, the use of the HPLC chromatographic method, preferably including LLS and RI-based detectors allows implementation of such indices. Furthermore, the ability to isolate the AHS present in these iron-complexes reinforces the practical application of the method.

Since the AHS, referred to as the primary reference standard for iron-saccharidic complexes, can begin to degrade shortly after synthesis or manufacture it can also be useful to establish a secondary reference standard. In practical terms, the secondary reference standard is based on the relative occurrence of iron aggregate derived from the active hematinic species compared to the total amount of iron aggregate capable of being released by the active hematinic species under set conditions over time. The measurement of iron aggregate is justified for establishing such benchmarks of active hematinic species integrity and stability because detectable iron aggregate levels are formed at the expense of the primary reference standard. The $[AHSAP_{TAM}]/[AHSAP_{TOTAL}]$ ratio plotted versus time after iron-saccharidic complex manufacturing or commercial release, provides an index of product storage stability. The time required to reach an arbitrary or performance-related ratio, e.g., 0.5, based on the HPLC signal quotient of $[AHSAP_{TAM}]/[AHSAP_{TOTAL}]$ can be especially useful, although any ratio can be selected as a guardrail to ensure active hematinic species product quality. Whatever ratio is selected to serve as a minimum acceptable standard to monitor clinical efficacy, utility and safety based on historical use will set the compositional standard for the secondary reference standard. Such a primary reference standard or a secondary reference standard, can be prepared as practical analytical standards for use in monitoring inter- and intra-laboratory or manufacturing performance and as a product quality index and product standardization tool.

The separated AHS-containing composition, Fraction 1, comprising the primary reference standard can be dried for extended storage and reconstituted for parenteral use and additional study.

Dried and/or reconstituted AHS can be stored for purposes of advanced analytical characterization, for example, in order to establish more definitive chemical criteria, as well as archiving AHS samples for future reference. Storage of the separated and lyophilized AHS is important because iron-saccharidic complexes are subject to destabilization and decomposition following their synthesis, particularly when such complexes remain in a diluent or liquid, particularly aqueous, carrier. In contrast, the dried AHS can be stored for extended periods of time, preferably in a moisture-free environment, including sealed containers. Furthermore, the dried, stable complex can be conveniently transported and reconstituted when needed at the point of use, thereby further extending its stability until just prior to use. For example, the dried AHS can be sealed in moisture proof containers such as metal foil pouches or glass containers, and stored at ambient temperature (about 20° C. to about 25° C.) or below for extended periods of time. For example, the dried complex can be stored from shortly after manufacture, such as from about one week thereafter, as well as after a moderately short storage period of about 6 months to for as long as about five years or more after manufacture; extended storage can be from about 1 year to about five years; or from about 1 year to about 3 years. During such post-manufacture storage, the AHS can be monitored for stability by comparison of the analytical properties, e.g., the chromatographic signature obtained using HPLC in combination with LLS and RI, of a reconstituted sample to a primary reference standard.

The isolated AHS (Fraction 1), as initially made or at any particular time thereafter, can be freeze dried (lyophilized) and reconstituted for ease of storage and transportation as well as for additional study. As a prerequisite to lyophilization, the iron-delivery vehicle or AHS present as an iron-saccharidic complex is preferably separated from its coexisting hydrophilic and other excipients as described previously. Such excipients include excess synthesis reactants, reaction byproducts, waste glucans, polyglucans, saccharidic lactones, degradation byproducts and other substances. In a preferred embodiment, the AHS is separated, in the manner of the primary reference standard species, comprising Fraction 1. By virtue of separating the AHS from coexisting hydrophilic substances, there is an increase in the $A_w$ value of the fraction or composition in which it is present; in other words, the $A_w$ value approaches 1.0 in the AHS containing fraction.

Freeze drying technology is well known in the food processing industry and has also been employed in the drying of pharmaceuticals. The technology is typically applied in order to dry compositions that are water-wet, although it is feasible to dry materials or solutes that are dispersed or dissolved in other diluents or solvents, alone or in admixture, for example, with water, and that are susceptible to freeze drying. Generally, the composition is frozen to a temperature significantly below 0° C. and subjected to a low absolute pressure, in other words, a high vacuum. Heat is carefully introduced in order to cause the ice to sublime. The process has been used to protect heat sensitive materials from thermal damage as well as to prevent shrinkage of porous materials during drying, so that they can be quickly and fully rehydrated. The present invention provides a method for the separation and lyophilization or freeze drying concentration of active hematinic species manufactured for use as parenteral iron delivery vehicles.

During freeze drying, a changing state of unbalance exists between ice in the frozen composition, referred to as product ice, and system pressure and temperature conditions. The migration of water vapor from the product ice interface occurs only if this state of unbalance exists and the product ice is at a higher energy level than the rest of the system. Freeze drying equipment is designed to present a set of controlled conditions effecting and maintaining the preferred temperature and pressure differences for a given product, thereby causing the product to be dried in the least amount of time.

The limit of unbalance is determined by the maximum amount of heat which can be applied to the product without causing a change from solid to liquid state (referred to as melt-back). This may occur even though the chamber pressure is low since the product dries from the surface closest to the area of lowest pressure; this surface is called the ice interface. The arrangement of the drying, solid composition or particles above this interface offers resistance to the vapors released from below, thereby raising the product pressure and temperature. To avoid melt-back, heat energy that is applied to the product closely approximates, and preferably does not exceed, the rate at which water vapor leaves the product. Another factor affecting the process is the rate at which heat energy applied to the product ice (and carried away by the migrating vapors) is removed by the condenser refrigeration system. By maintaining a low condenser temperature, water vapor is trapped as ice particles and effectively removed from the system, thereby reducing and simplifying the vacuum pumping requirement. Air and other noncondensible molecules within the chamber, as well as mechanical restrictions located between the product ice and the condenser, offer additional resistance to the movement of vapors migrating towards the condenser.

Four conditions are generally considered essential for freeze drying. These process conditions are as follows: (1) the product is solidly frozen below its eutectic point or glass transition temperature; (2) a condensing surface capable of reaching temperatures approximately 20° C. colder than the ice interface temperature is provided, typically less than about −40° C.; (3) the vacuum system is capable of evacuation to an absolute pressure of from about 5 to about 65 microns of Hg (about 0.5 to about 10 Pa; preferably from about 1 to about 8 Pa); and, (4) a source of heat input to the product, controlled at from about −60° C. to about +65° C.; preferably from about −40° C. to about +65° C.; more preferably from about −30° C. to about +55° C.; most preferably from about −25° C. to about +25° C.; typically, a temperature of about +20° C. is employed to provide the heat required to drive water from the solid to the vapor state (i.e., the heat of sublimation). The physical arrangement of equipment designed to satisfy these four conditions varies widely, and includes individual flask freeze drying apparatus and batch process freeze drying apparatus. Freeze drying processes are typically carried out in chambers on a batch basis when exacting control of the process is required, such as in the chemical and pharmaceutical industry. This allows an operator to more precisely control what occurs to the product being sublimed. Suitable equipment is described, for example, in U.S. Pat. No. 6,122,836 (assigned to the Virtis Division of S.P. Industries, Inc., N.Y.) and references cited therein, as well as Zapsalis and Beck, Food Chemistry and Nutritional Biochemistry, 1985, Chapter 1, pp. 23-26 (all of which are incorporated herein by reference to the extent permitted). Other suitable commercial equipment and process conditions are described in detail in the section entitled "Freeze Drying", van Nostrand's Scientific Encyclopedia, Eighth Edition, pages 1338-1342, 1995 (incorporated herein by reference to the extent permitted).

The effectiveness of freeze drying processes is partially dictated by the triple point curve for water where solid water in the form of ice undergoes a direct transformation into the vapor phase at temperatures of less than 0° C., and pressures of less than 4.58 Torr (610.5 Pascals). Efficient freeze drying is conducted under a pressure (vacuum) of from about 10 microns to about 200 microns Hg; preferably from about 40 to 100 microns; more preferably from about 40 to about 80 microns; typically a pressure of about 60 microns is used. The removal of water molecules existing as (a) ice within a hydrated physical matrix or (b) ice that develops from freezing simple aqueous solutions, ideally gives a dry residual physical matrix free of water or a residue of some desired water-free solute. However, where hydrophilic solutes, colloids, suspensions or dispersions exist within an ice system, such as saccharidic excipients, they can concentrate within the ice structure as the ice is subjected to the freeze drying process and the volume of solvent or diluent water is reduced. Since such materials become more concentrated as the freeze drying progresses, this increasingly depresses the freezing point of the frozen aqueous system. As this condition proceeds, the colligative properties of solute interaction with water can also rise above the eutectic point, contributing to or causing a melt-back phenomenon. This is contrary to the preferred freeze drying process of the present invention in which the ice accompanying the desired solute, the AHS, is maintained in a frozen state, substantially unimpaired by hydrophilic solute species that may include difficult-to-remove water, until substantially all water associated with the AHS has been removed by sublimation.

The preferred freeze drying of the AHS is accomplished, in significant part, as a result of the high $A_w$ of the fraction (Fraction 1) comprising substantially all of the iron-saccharidic complex originally present in the sample, which facilitates its rapid shell-freezing onto a plate, the walls of a container or some other three-dimensional scaffolding that ensures a high surface to volume ratio for the frozen fraction. The more efficiently that shell-freezing occurs, the better the quality of the lyophilized product. Freezing is typically carried out at temperatures of from about −160° C. to about −10° C.; preferably from about −80° C. to about −20° C.; for example about −60° C. When the AHS is present in a frozen composition where the water displays an $A_w$ value approaching 1.0, pressures below about 4.58 Torr (610.5 Pa) result in increased water vapor pressure and temperature conditions as described can result in an increased water vapor pressure and efficient sublimation. Water is removed from ice by maintaining the pressure surrounding the frozen AHS below the vapor pressure on the surface of remaining ice, removing the water vapor with a vacuum pump and condensing it on refrigerated surfaces held at temperatures of from about −120° C. to about −25° C.; preferably from about −80° C. to about −50° C.; typically −60° C. In particular, the high $A_w$ of the previously separated AHS facilitates the migration rate of the sublimation front throughout the frozen product. In the absence of removing the excipients, particularly hydrophilic excipients, from the AHS or iron-saccharidic complex, the AHS is subject to melt-back during the freeze drying process. In other words, the presence of hydrophilic substances results in water being sufficiently bound or retained by the AHS composition in which such hydrophilic substances are present. If higher temperatures are employed to increase the vapor pressure in an effort to remove such bound water, this also can have the undesirable effect of causing the ice phase to melt, thereby impairing freeze drying. Consequently, it is preferred that all or substantially all of the hydrophilic excipients be removed or separated from the AHS prior to freeze drying: preferably greater than about 95% of those originally present are removed; more preferably greater than about 98%; still more preferably greater than about 99%; most preferably greater than about 99.9% are removed; for example, the AHS is separated from hydrophilic excipients prior to freeze drying to the extent that such excipients are present in trace amounts.

For purposes of the present invention, the dried AHS residue comprises the pharmacologically useful iron-saccharidic complex. Thus, the separated and dried AHS is suitable for further analytical study or, optionally, reconstitution, in order to meet other investigative analytical or pharmacological uses. Typically, the methods of the present invention are suitable for drying AHS, from which excipients have been substantially removed, such that from about 85% to at least about 99%; preferably from about 90% to at least about 97%; most preferably from about 92% to at least about 95% of the water has been removed. It should be appreciated that a small percentage of the water originally present in the separated AHS may be associated, or strongly bound, to the AHS and attempts to remove such bound water may pose a danger of unnecessarily degrading the AHS. A sample of post-lyophilized and reconstituted AHS subjected to LLS and RI-based HPLC analysis, is illustrated in FIG. 10. The figure shows a chromatographic signature substantially identical to that in FIG. 1, which serves as the primary reference standard. Moreover, the analytes depicted in FIGS. 1 and 10 are essentially identical to the AHS seen in FIG. 3 where excipients were allowed to remain.

A hematinic material with an HPLC profile that is different from the primary reference standard such as in FIG. 1, or in FIG. 10, is one that also shows evidence of the AHSAP in the lyophilized product having an unusual morphology. When the AHSAP is observed to be present as part of the AHS in the course of HPLC studies, the microscopic appearance of the lyophilized AHS at 100-fold magnification and higher, can be visually described as a corduroy-type structure. It displays red-brown parallel bands or wales of ferric iron uniformly interspaced with transparent bands of thin carbohydrate plates. The red-brown parallel bands of ferric iron have a distinct columnar shape, parallel to each other, that are at least twice the diameter of the thickness displayed by the long planar transparent carbohydrate plates that are repeatedly interspaced between them. This observed microscopic form has structural analytical significance that corresponds to HPLC light scattering data when chromatographic profiles appear as those seen in FIGS. 4-9. When a desirable freshly prepared AHS corresponding to the primary reference standard of iron-saccharidic complexes is present, the morphology of the lyophilized product is characteristically different in that there is an absence of columnar structure.

Preservation of the lyophilized product can be maintained in a vacuum or under any inert gas, including, for example, nitrogen, argon and helium (as well as any gas that is not reactive with the lyophilized product) before it is reconstituted for analysis or use. Also, since the lyophilization process alone does not compromise the structure of iron-saccharidic complexes, use of the process has value for maintaining these hematinic agents at various time intervals so as to document the hematinic species present at a given point in time when lyophilization was implemented. This provides a method for archival storage and documenting of product manufacture and quality. In other cases, lyophilization can be specifically used to stabilize and store primary and/or secondary reference standards of these hematinic compositions. Furthermore, suitably prepared and maintained lyophilized AHS can be safely stored until needed with little risk of significant degradation of the product. Furthermore, the product in such a form can be conveniently shipped to geographically remote locations and conveniently stored until needed, at which time reconstituting the hematinic for parenteral use is readily accomplished. For example, the lyophilized product prepared according to the present invention can be stored in sealed glass or appropriately protected metal containers, preferably topped with a substantially moisture free inert gas. Alternatively, such product can be sealed in a metal foil pouch in a quantity suitable for reconstituting as a single parenteral dose, etc. The iron-saccharidic complexes referred to are prepared in order to produce parenteral hematinic complexes for the delivery of iron to humans or animals in need thereof. These iron complexes generally occur in a form such that iron can be parenterally and benignly administered to augment hematopoietic mechanisms required for the management of numerous clinical conditions in mammals, particularly in human beings in need thereof.

Parenteral administration of a substance, e.g., a drug or the AHS of the present invention, refers to introduction into the body by some means other than through the gastrointestinal tract. In particular, it includes, intravenous, subcutaneous, intramuscular or intramedullary injection or short, e.g., about 5 minutes, or prolonged infusion, e.g., about 30 minutes or longer. Parenteral routes of administration can provide benefits over oral delivery in particular situations. For example, parenteral administration of a drug typically results in attainment of a therapeutically effective blood serum concentration of the drug in a shorter time than is achievable by oral administration. This is especially true of intravenous injection, whereby the drug is placed directly in the bloodstream. Parenteral administration also results in more predictable blood serum concentrations of the drug, because losses in the gastrointestinal tract due to metabolism, binding to food and other causes are eliminated. For similar reasons, parenteral administration often permits dose reduction. Parenteral administration is generally the preferred method of drug delivery in emergency situations, and is also useful in treating subjects who are uncooperative, unconscious, or otherwise unable or unwilling to accept oral medication. With regard to hematinics, parenteral administration of the AHS is particularly useful for patients undergoing dialysis treatment since it can be administered concurrently.

As described above, the separated AHS can be lyophilized and stored as a freeze-dried composition. Thereafter an injectable solution can be prepared by reconstitution of the composition. Furthermore an article of manufacture can be produced comprising a sealed container such as a vial, ampoule or pouch having contained therewithin a unit dosage amount of the composition in a sterile condition. Such an article can be used for treating or preventing an iron deficiency disorder in a subject, the method comprising (a) reconstituting a unit dosage amount of the composition in a physiologically acceptable volume of a parenterally acceptable solvent liquid to form an injectable solution, and (b) injecting the solution parenterally into the subject. At the time that the AHS is reconstituted for parenteral use, additional agents or excipients can be added in controlled amounts in order to provide a suitable parenteral solution. Such agents include, for example, buffering agents, pH modifiers, preservatives, tonicity adjusting agents, etc. Alternatively, one or more of such agents can be included in an appropriate amount in dry or powder form with the lyophilized AHS such that when the AHS is reconstituted for parenteral use, the resulting parenteral composition includes the necessary materials to form a suitable parenteral composition for immediate use. Alternatively, only the buffering agent is present and other agents are added to the extent required.

One or more active hematinic species selected from those disclosed hereinabove are present in a reconstitutable powder composition of the invention in a total amount of about 30% to about 95%, alternatively about 40% to about 90%, or about 50% to about 85%, by weight of the composition.

When used, the buffering agent is present in an amount of about 5% to about 60%, preferably about 10% to about 60%, and more preferably about 20% to about 50%, by weight of the composition, and is typically the predominant excipient ingredient. In one embodiment of the invention, the reconstitutable powder composition consists essentially of the AHS and the buffering agent.

The buffering agent is selected to provide a pH of the composition, upon reconstitution in a physiologically acceptable volume of a parenterally acceptable carrier or solvent liquid, that (a) is parenterally acceptable, (b) is consistent with the AHS being in solution or sufficiently dispersed so as not to cause an unacceptable adverse reaction, in the carrier or solvent liquid, and (c) provides a medium wherein the AHS exhibits acceptable chemical stability for at least about one hour following reconstitution so as to facilitate parenteral administration. Suitable buffering agents can illustratively be selected from sodium and potassium phosphates, sodium and potassium citrates, mono-, di- and triethanolamines, 2-amino-2-(hydroxymethyl)-1,3-propanediol (tromethamine), etc. and mixtures thereof. Preferred buffering agents are dibasic sodium and potassium phosphates and tromethamine. An especially preferred buffering agent is dibasic sodium phosphate, for example dibasic sodium phosphate anhydrous, heptahydrate, dodecahydrate, etc.

In one embodiment, the pH of the composition upon reconstitution is about 7 to about 9, preferably about 7.5 to about 8.5, for example about 8. If desired, pH can be adjusted by including in the composition, in addition to the buffering agent, a small amount of an acid, for example phosphoric acid, and/or a base, for example sodium hydroxide.

Excipients other than the buffering agent, if present, constitute not more than about 10%, preferably not more than about 5%, by weight of the composition prior to reconstitution. For purposes of this discussion, the term excipient does not include water. In one embodiment of the invention, no excipients other than the buffering agent are substantially present.

Optionally, one or more preservatives can be included in the composition at up to about 0.5% by weight. Suitable illustrative preservatives include methylparaben, propylparaben, phenol and benzyl alcohol.

An injectable solution composition prepared by reconstituting a powder composition as herein provided in a parenterally acceptable liquid carrier or solvent, preferably an aqueous solvent, is a further embodiment of the present invention. Any known parenterally acceptable liquid carrier or solvent can be used to reconstitute a powder composition of the invention. Water for injection can be suitable, but will generally provide a hypotonic solution. Accordingly, it is generally preferred to use an aqueous liquid containing a solute such as sodium chloride and/or possibly dextrose. Illustratively, 0.9% sodium chloride injection USP, sterile 0.9% sodium chloride injection USP, 5% dextrose injection USP, and 5% dextrose and 0.45% sodium chloride injection USP are suitable.

A suitable volume of the liquid carrier or solvent for reconstitution depends on the age and body weight of the subject, the solubility and dosage amount of the AHS and other factors, such as whether the parenteral composition is to be administered by injection, IV push or IV.

In this process, AHS and dibasic sodium phosphate heptahydrate as buffering agent are dissolved in water to form an aqueous solution or composition. Preferably water for injection is used as the solvent. AHS and the buffering agent are present in the solution at concentrations relative to each other consistent with the desired relative concentrations of these ingredients in the final composition. Absolute concentrations of these ingredients are not critical; however, in the interest of process efficiency it is generally preferred that the concentration of AHS be as high as can be conveniently prepared without risking exceeding the limit of solubility to the extent of forming an unsuitable aggregate. Other parenteral formulation ingredients or agents as described above can be added in this step if desired. Order of addition is not critical An article of manufacture comprising a sealed vial, preferably a glass vial, having enclosed therewithin a powder composition as herein provided in a unit dosage amount and in a sterile condition, is a further embodiment of the present invention. In a particular embodiment, such an article of manufacture is provided, prepared by a process as described above. The vial preferably has a capacity sufficient to enable reconstitution of the composition in situ. Generally a capacity of about 1 ml to about 10 ml, preferably about 2 ml to about 5 ml, will be found convenient. The term "vial" herein is used to denote any small container, having a closure, that is suitable for packaging a unit dosage amount of a reconstitutable powder, preferably in a sterile condition. It will be understood that equivalent forms of packaging, such as an ampoule, a disposable syringe and a syringe cartridge, are encompassed by this embodiment of the invention.

The present invention is further directed to a therapeutic method of treating a condition or disorder where treatment with a hematinic is indicated, the method comprising parenteral administration of a reconstituted composition of the invention to a subject in need thereof. The dosage regimen to prevent, give relief from, or ameliorate the condition or disorder preferably corresponds to any suitable interval in accordance with a variety of known factors. These include the type, age, weight, sex, diet and medical condition of the subject and the nature and severity of the disorder. Thus, the dosage regimen actually employed can be varied.

A typical preparation comprising an AHS prepared according to the process of the present invention and provided in a suitable container, e.g., an ampoule, vial or pouch, generally contains sufficient AHS so as to provide, upon reconstitution, about 5 to 100, e.g., about 7 to about 50, typically about 10 to about 40 mg iron per mL.

A parenteral AHS in the form of sodium ferric gluconate can be produced in a composition equivalent to that of a presently available commercial product, for example, in the presence of sucrose. Consequently, the composition can be administered in a dosage form and based on an administration schedule equivalent to that currently recommended. The dosage is typically expressed in terms of the mg content of elemental iron. For example, the recommended dosage for repletion of iron deficiency in hemodialysis patients is equivalent to 125 mg of iron for a single administration. The product, when provided in the form of a 5 mL ampoule for intravenous injection containing 62.5 mg (12.5 mg/mL) of elemental iron and also containing approximately 20% sucrose w/v (195 mg/mL) in water at a pH of 7.7-9.7, can be administered as a 10 mL dose; equivalent to 125 mg of elemental iron. For slow IV administration (undiluted), 125 mg can be introduced over 10 minutes; for IV infusion (diluted in 0.9% NaCl), 125 mg in 100 mL over 60 minutes. A physician trained in the art can determine the appropriate total dosage needed by a patient based on the medical and physical condition of the patient and the iron improvement required. For example, in order to achieve a favorable hemoglobin or hematocrit response, the current recommendation for the commercial hematinic of the above type is a minimum cumulative dose of 1.0 gram of elemental iron, administered over eight sessions at, e.g., eight sequential dialysis treatment sessions.

Dosage and administration of a parenteral product based on another currently available commercial product in the form of sodium ferric hydroxide in sucrose is also described in the art. Dosage of this form is also typically expressed in terms of elemental iron content. Typically each 5 mL vial of the composition contains 100 mg of elemental iron based on 20 mg/mL. Repletion treatment of iron deficiency in hemodialysis patients is typically 5 mL comprising 100 mg of elemental iron delivered intravenously concurrent with dialysis. Patients typically require a total of 1 gram (1,000 mg) of elemental iron administered in conjunction with 10 sequential dialysis sessions for an appropriate hemoglobin or hematocrit response. Maintenance of appropriate levels of hemoglobin, hematocrit and other laboratory criteria may be determined by a skilled physician, as appropriate.

The term "about" when used as a modifier for, or in conjunction with, a variable is intended to convey that the numbers and ranges disclosed herein are flexible and that practice of the present invention by those skilled in the art using temperatures, concentrations, amounts, contents, carbon numbers, properties such as molecular weight, viscosity, solubility, etc., that are outside of the range or different from a single value will achieve the desired result, namely preparation of a hematinic iron-saccharidic complex suitable for freeze drying, the highly purified hematinic iron-saccharidic complex produced thereby and methods for its use. Furthermore, where a range of values is expressed, it is to be understood, unless otherwise expressed, that the present invention contemplates the use of the other ranges that are subsumed within the broadest range.

Examples

For purposes of the present invention, reference to water content of an undried substance or composition, in other words, prior to being dried, is given as a percentage of the total weight of the undried substance or composition. Water content of a dried substance or composition is given as a percentage of the total weight of dry matter only, excluding all moisture.

Following is the procedure for low pressure gel permeation chromatography used in preparing the samples for which test results appear in FIGS. 1, 2 and 10, including preparation of purified, substantially excipient-free AHS. The specific application of low pressure gel permeation chromatography (GPC) for AHS separation employs crosslinked polyglucans or dextrans displaying molecular weight exclusion characteristics greater than about 5,000 and preferably greater than about 1,500 Daltons. The stationary GPC phase is "Sephadex G-10" (Amersham-Pharmacia Biotech, Piscataway, N.J.). A solvent reservoir supplies a mobile phase of HPLC grade water by gravity or metered flow to a GPC column containing the stationary dextran phase. The column is constructed of glass having a 2.0 cm diameter and a length of 25 cm. The stationary phase is prepared according to manufacturer recommendations including hydration of the dextran and vacuum degassing before use. A 400 microliter sample volume of the hematinic solution, including the iron-saccharidic complex, for example, as released by its manufacturer in sealed glass ampoules, is fed to the top of the GPC column and allowed to permeate into the stationary phase. Once the highly colored hematinic solution has penetrated into the stationary phase, HPLC grade water is supplied manually or by pump at 1-4 mL per minute so as to ensure its elution as a well-defined color band through the column. When the characteristically colored AHS has eluted from the column as determined by minimal spectrophotometric absorption at 430 nm this marks the end of elution for Fraction 1. A more refined analytical method for finding a separation point for Fraction 1 and the beginning of the subsequent fraction identified herein as Fraction 2 uses the anthrone reaction (Dreywood, 1946 cited previously). The eluate boundary between the two Fractions can be defined because the lowest concentration of furfural-producing carbohydrates in the overall eluate flow of the partitioning process occurs between the AHS and its hydroscopic excipients. In practice, 100 microliter samples of the eluate flow are sampled, reacted with anthrone reagent and the resulting 620 nm absorbance is recorded. The red-brown colored Fraction 1 contains the AHS substantially free of hydrophilic and highly hydroscopic excipients that formerly coexisted with the AHS as released. Remaining volume eluted from the column is regarded as Fraction 2.

The AHS obtained, for example, from Fraction 1 as described above, or from samples taken directly from glass ampoules of hematinic compositions distributed for use in clinical applications or samples prepared from concentrated volumes of Fraction 1, including reconstituted compositions based on the use of freeze drying, can be further analyzed with the use of HPLC-based refractive index (RI) and laser light scattering (LLS) analysis. Specifically, the method uses a Waters 590 pump (Waters Corporation, Milford Mass.) to supply an aqueous mobile phase to a 7.8 mm diameter by 30 cm long GMPW$_{XL}$ column (Tosoh Biosep, Montgomeryville, Pa.). The internal column support material is comprised of polymethylmethacrylate backbone eliminate polymer beads having a 13 micron diameter particle size with a various pore sizes in the range of from less than about 100 Angstroms to about 2000 angstroms. The column eluant stream is monitored by a Wyatt miniDawn multi-angle light scattering detector in combination with an Optilab DSP interferometric refractometer (both from Wyatt Technology, Inc., Santa Barbara, Calif.). The column heater and refractometer operating temperatures were held at 35° C. The aqueous mobile phase included 200 parts per million sodium azide, pH was adjusted to 6.0 and was subjected to 0.02 micron vacuum filtration and an ebullient helium sparge before being used. The mobile aqueous phase was supplied to the system at a flow rate of 1.0 mL per minute with a pressure of 150 pounds per square inch. Preparation of a sample for testing requires 0.02 micron filtration through a membrane filter (for example, "Anotop" filters, Whatman, Maidstone, England). As hematinic compositions, iron-saccharidic complexes or components thereof age, membrane filters up to 0.45 microns may be required in order to remove larger particulates without clogging. If particulates are not eliminated from analytical samples before injection into the HPLC system, HPLC analytical performance will be severely corrupted. Samples are diluted as desired up to 2.5% weight by weight and a 80 to 200 microliter sample volume is injected into the HPLC system for analysis. For multiple sample analyses, automation is facilitated by use of "Water's autosampler", model 717 (Milford, Mass.).

The combination of RI and LLS detection with HPLC establishes an absolute macromolecular weight for analytes that produce a chromatographic peak as well as a root mean square (rms) radius value also referred to as a radius of gyration (Rg). The rms value coupled with absolute weight determination provides insight into the shapes of light scattering species, such as rods, coils, spheres or discs. The formula weight of the AHS and shape of specific iron-saccharidic complexes can be used for various monitoring purposes.

The freeze drying process used for the examples of the present invention is as follows:

Fraction 1, identified above, serves as the starting material for freeze drying. Using the method described below, volumes as small as 10 mL or as large as 100 mL and comprising the AHS can be readily freeze dried provided that the sample is substantially free of saccharidic substances that tend to decrease the entropy of water and its vapor pressure. These volumes can be contained in any glass container that will withstand the physical stress of shell freezing, which method is used to expedite the overall dehydration and concentration of the AHS. The preferred ratio of liquid volume to the container volume for shell freezing is from about 1 to about 5, but other ratios are feasible. After liquid containing the substantially excipient-free AHS is introduced into the container, the container is rotated at about 50 revolutions per minute in a cryogenic bath. The bath can be made by mixing dry ice and acetone or, alternatively, liquid nitrogen can be used, provided that a temperature of at least about −50° C. or lower is maintained. The immersion and rotation of the container freezes the AHS-containing aqueous volume onto the walls of the container. This increases the surface to volume ratio of the AHS-containing aqueous volume so as to expedite water sublimation. Other process and equipment variations of this procedure can be used to obtain the same or similar results.

One or more containers of shell-frozen compositions comprising water and AHS are situated on a shelf within a freeze dryer. An instrument such as a "Virtis Unitop 600L" linked to a "Freezemobile 12 ES" (Gardiner, N.Y.) can be used for this purpose. A vacuum of 60 microns of Hg (7.5 Pa) was maintained in the system and a condenser temperature of at least about −60° C. or colder was maintained. A preferred freeze drying cycle was as follows: initial shelf holding temperature of −50° C. for 2 hours; temperature ramped up to 25° C. over a 12 hours; sample soak at 25° C. for an additional 24 hours. Preferably the dried product should be stored under desiccating storage conditions, for example under a dry, inert gas such as argon or nitrogen. The dried AHS can be reconstituted with a desired aqueous volume whereupon it readily goes into a solution and can be readily filtered through a 0.02 micron membrane, as described above.

HPLC analysis using RI and LLS detection is demonstrated in the following 10 examples using iron-saccharidic complexes. The results for each of samples 1 through 10 corresponds to FIGS. 1 through 10. The hematinic samples 1-4 and 6-10 are the iron-saccharidic complex identified as sodium ferric gluconate complex in sucrose (SFGCS), sold under the brand name Ferrlecit® (manufactured by Rhône-Poulenc Rorer, Dagenham, Essex, England). Sample 5, and its corresponding FIG. 5, is ferric hydroxide sucrose complex (FHSC), sold under the brand name Venofer® (manufactured by Luitpold Pharmaceuticals, Shirley, N.Y.). Samples used for HPLC analysis were taken from newly opened glass ampoules stored at room temperature conditions. Additionally, samples 6, 7, 8, and 9 were analyzed after 6, 12, 22 and 25 months following manufacturing release of the product. These time periods are referred to herein as "time after release", TAM and correspond to TAM$_{\#1}$, TAM$_{\#2}$, TAM$_{\#3}$ and TAM$_{\#4}$ in the examples. Samples were prepared by a 1 to 20 dilution and 200 microliters sample volumes of these dilutions were analyzed by the HPLC method specified above.

Example 1 test results are shown in FIG. 1. The results are based on the use of HPLC with RI and LLS detection for evaluating an AHS isolated in the Fraction 1 eluate obtained using preparative low pressure GPC and a sample of iron-saccharidic complex as obtained from its glass distribution ampoule. The single well defined chromatographic profile for the LLS signal and the RI signal coincide for AHS elution but no other excipients appear in the purified material.

Example 2 results are shown in FIG. 2. The results are based on the use of HPLC with RI and LLS detection for evaluating the AHS isolated in the Fraction 2 eluate obtained from using preparative low pressure GPC and the iron-saccharidic complex of Example 1. It is clear from these two results that the excipients and AHS are separated or isolated in distinct fractions. 15 microliters of AHS from Fraction 1, Example 1 was added to the Fraction 2 eluant as an internal standard in order to identify where its elution position would appear relative to that of the excipients.

Example 3 results are shown in FIG. 3. The results are based on the use of HPLC with RI and LLS detection, applied to the same hematinic sample as in Example 1, to substantially separate Fraction 1 with its characteristic AHS, from excipients usually observed in Fraction 2. The HPLC method can discern the various iron-saccharidic complex constituents of a hematinic composition on a single chromatographic profile. While HPLC is particularly suited to rapid analytical testing, low pressure chromatography is particularly suited as a preparative method for the preferred AHS. The LLS signal for the AHS corresponds to the observed RI signal.

Example 4 results are shown in FIG. 4. The results are based on the use of the preferred HPLC method for detecting structural deviations from the original AHS. In its undegraded form, the AHS serves as a quality benchmark also denoted in these Figures as a "primary reference standard". HPLC analysis using RI and LLS was carried out on a hematinic composition obtained directly from its delivery ampoule and comprising an iron-saccharidic complex. The figure shows inconsistencies in the expected, or ideal, AHS peak. Note the appearance of a new, observable chromatographic secondary peak adjoining that of the AHS primary reference standard. This feature is indicative of iron aggregate species as a consequence of AHS degradation. The figure identifies the second peak as an active hematinic species aggregate peak (AHSAP) using LLS detection. It is particularly noteworthy that this peak is not observed using RI detection alone.

Example 5 results are shown in FIG. 5. The results are based on the use of HPLC equipped with RI and LLS detectors. This figure also shows structural changes in the AHS, or primary reference standard peak, of hematinic comprising FHSC. The sample of this product included a manufacturing date of December 1999 on the ampoule and an expiration date of December 2002. In this example, the AHSAP appears as a shoulder on the AHS peak, suggesting a different degree of change compared with the sample studied in Example 4. While LLS and RI chromatographic profiles generally overlap, only the LLS signal detects evidence of iron aggregates in the parenteral hematinic. As in each previous example, the sample for this study was obtained directly from a sealed glass ampoule used for clinical distribution.

Examples 6-9. Readily detectable departures in the HPLC based RI and LLS elution profiles from the expected chromatographic profile for an AHS reflect either a departure from preferred manufacturing conditions or degradation of AHS due to aging and destabilization while still sealed in glass delivery ampoules. The destabilization reflects itself in the aggregation of iron normally embodied as a constituent of the desirable AHS structure. Although HPLC with RI detection fails to detect the changes in the iron-saccharidic complexes, LLS detection clearly provides evidence of such product destabilization. The advantages of the invention as a method for monitoring the state of a hematinic product comprising iron-saccharidic complex is illustrated where HPLC is coupled with RI and LLS detectors in order to detect evidence of degradation of the AHS as indicated by iron aggregate formation. Iron aggregate formation is observed as the HPLC chromatographic peak denoted as AHSAP. Individual samples of iron-saccharidic complexes, specifically SFGCS, manufactured over the course of several months were stored at room temperature in the absence of light and without any excursions known to stress the stability of the products while sealed in their glass ampoules. The samples were aged at room temperature in the dark and after 6, 12, 22 and 25 months following their manufacture, the respective ampoules were opened and the contents analyzed by HPLC with RI and LLS, as described. None of the stored product samples had reached its stated expiration date stated on the packaging material. The sample with the shortest TAM value of 6.0 months was designated as $TAM_{\#1}$ and that with the longest storage of 25 months $TAM_{\#4}$. The results of HPLC studies applied to this range of successively aged hematinic examples are shown in FIGS. 6-9. The key area of analytical interest in the chromatographic profiles presented in FIGS. 6-9 is the region where the AHS signature appears, thus only that specific elution range pertinent to the RI and LLS analytical profile is shown.

Taken as a group in sequence from TAM#1 (FIG. 6) through TAM#4 (FIG. 9), it is apparent that the RI signal from these samples show little effect of sample aging by way of AHS decomposition and iron aggregation. On the other hand, evidence of AHS destabilization with iron aggregation is prominently seen by the AHSAP shoulder or a secondary peak, which was detected by using LLS in all four samples.

By way of these examples, it is evident that the preferred HPLC based RI and LLS method provides an ability to verify the presence of an AHS or its coexistence with normally occurring excipients with which it is released for parenteral use. Beyond this, the method affords a significant ability to monitor, as well as to investigate and develop, hematinics based on iron-saccharidic complexes as a group. It can be seen that this class of hematinics is susceptible to destabilization resulting in iron aggregates that are commingled with the preferred or normal AHS. Unless HPLC is used with at least LLS detection as well as RI detection, the occurrence of iron aggregates can go unnoticed in these hematinic agents.

As described above, when carrying out the preferred method of this invention, samples are routinely filtered through a 0.02 micron Anotop brand membrane filter to avoid operational problems with the sample before it is injected into the HPLC. Iron-saccharidic samples that show no evidence of AHSAP occurrence can be readily filtered in preparation for study but older samples filter with great difficulty or not at all even using 0.45 micron filters. It has been observed that difficulties in the preparatory filtration of samples for HPLC study according to the specified and preferred method correspond with the occurrence of the highest levels of AHSAP. The measurable and quantitative entrainment of iron aggregates over a membrane filter surface can provide another, albeit cursory, method for evaluating the unintended degree of hematinic breakdown. However, application of such a filtration method to a hematinic before parenteral use would be impractical and, furthermore, it would not have any effect on degraded AHS that had not progressed to the filterable iron aggregate stage. When significant amounts of iron aggregates develop in samples and hematinic analysis is essential, sample filtration is necessary for HPLC instrument performance and maintenance. Also, it should be noted that if a residue of iron aggregate or other particulate material is entrained on a membrane filter as a result of preparing AHS for HPLC analysis, the quantitative amount of aggregate on the filter should be considered together with HPLC analysis as complementary indicators of product decay. Where little or no evidence of filterable material is present in hematinics and particulates have dimensions of less than 10 nm in diameter, the HPLC method more accurately serves as the preferred method for monitoring hematinic quality.

Example 10 results are shown in FIG. 10. This example involved the application of the preferred method for HPLC based RI and LLS analysis to an AHS that was reconstituted from a freeze dried state. While AHS isolated from an iron-saccharidic complex has never before been reported, its ability to be freeze dried and reconstituted without decomposition, degradation or iron aggregate formation was particularly uncertain. An original 2.5 mL sample volume of iron-saccharidic complex as released, SFGCS, taken from a sealed glass ampoule was separated into Fraction 1 and Fraction 2 according to the low pressure chromatography method for preparing substantially excipient free AHS. Fraction 1 containing the AHS was freeze dried as described above. One week after freeze drying it was reconstituted to its original volume (2.5 mL) with HPLC grade water. A 500 microliter volume of the 2.5 mL reconstituted solution was then diluted to 20.0 mL and 200 microliters of this was injected for HPLC based RI and LLS analysis as described. The resulting chromatographic profile is shown in FIG. 10. It is noted that both the LLS and RI signals not only overlap, consistent with the chromatographic profiles observed in FIG. 1, but there is no evidence of any iron aggregate formation or AHSAP as observed in FIGS. 6-9. By way of this example, HPLC with RI and LLS detection is also shown to be useful for monitoring the quality of freeze dried AHS.

Example 11 was carried out to compare the response to freeze drying of untreated versus treated hematinic. Three samples of an iron-saccharidic complex, SFGCS, as manufactured and comprising AHS, sucrose and residual excipients were subjected to freeze drying. All three samples originated from the same production batch as released in different glass ampoules. The freeze drying method used was the same as that applied to the hematinic in Example 10, but contrary to that example, the AHS was allowed to remain with its excipients during the course of freeze drying. The experimental objective was to observe whether or not there were any weight disparities in the final freeze dried product due to the presence of hydrophilic excipients compared to the same product freeze dried in the absence of such hydrophilic excipients. Results are summarized for the hematinic dried with its excipients in Table A.

TABLE A

| Sample No. | Sample weight (g) | Water removed (%)* | Freeze dried weight (g) |
| --- | --- | --- | --- |
| 1 | 10.414 | 77.3 | 2.373 |
| 2 | 10.330 | 79.9 | 2.169 |
| 3 | 9.481 | 78.2 | 2.070 |
| Mean ± sd | 10.075 ± 0.421 | 78.5 ± 1.1 | 2.204 ± 0.126 |

*Expressed as a percent of original sample weight

Three additional samples of the same hematinic batch from the same source as used in Table A were obtained from different unopened ampoules and subjected to treatment in a low pressure chromatographic column as described above. Fraction 1 of each sample (comprising the AHS, but without the associated hydrophilic excipients, including sucrose) was then subjected to freeze drying as described above; results are summarized in Table B:

TABLE B

| Sample No. | Sample weight (g) | Water removed (%)* | Freeze dried weight (g) |
| --- | --- | --- | --- |
| 1 | 9.500 | 93.50 | 0.613 |
| 2 | 7.840 | 93.70 | 0.498 |
| 3 | 3.200 | 91.47 | 0.273 |
| Mean ± sd | 6.847 ± 2.667 | 92.89 ± 0.10 | 0.461 ± 0.140 |

*Expressed as a percent of original sample weight

The test results clearly show that a significantly higher percentage of water is removed from the samples subjected to column separation and identical conditions of freeze drying.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A composition comprising an active hematinic species (AHS) for treating an animal, wherein said composition is substantially free of excipients having a molecular weight of less than about 5,000 Daltons.

2. The composition of claim 1 wherein said AHS comprises ferric hydroxide sucrose complex, sodium ferric gluconate complex or ferric saccharate complex.

3. The composition of claim 2 comprising greater than about 85 weight percent of AHS and, correspondingly, less than about 15 weight percent excipients having a molecular weight of less that about 5,000 Daltons.

4. The composition of claim 3 wherein said excipients are present at less than about 2 weight percent.

5. The composition of claim 1 wherein said excipients are present at less than about 5 weight percent.

6. The composition of claim 1 further comprising a solvent or diluent for said AHS or a mixture of solvent and diluent.

7. The composition of claim 6 wherein said solvent or diluent comprises water.

8. The composition of claim 1, said AHS having an absolute molecular weight of at least about 100,000 Daltons.

9. The composition of claim 8 further comprising a solvent or diluent or a mixture of solvent and diluent in admixture therewith, said mixture suitable for parenteral administration.

10. The composition of claim 9 wherein said solvent or diluent comprises water.

11. The aqueous composition of claim 10 wherein said AHS comprises ferric iron present at a concentration of 50-120 mg per 5.0 milliliters volume of said composition.

12. The composition of claim 1 wherein said excipients include byproducts and unreacted starting materials from the synthesis of said AHS, degradation byproducts, iron containing species having a molecular weight of less than about 5,000 Daltons and non-hematinically active components.

13. The composition of claim 12 wherein said non-hematinically active components include sucrose.

14. The composition of claim 1 wherein said composition is substantially free of excipients comprising aggregated iron-containing compounds.

15. The composition of claim 1 wherein: (a) said AHS is in powder form and comprises about 30% to about 95% by weight of said composition; (b) said composition further comprises a parenterally acceptable buffering agent in an amount of about 5% to about 60% by weight; and (c) said composition optionally comprises one or more parenterally acceptable excipient ingredients in a total amount of zero to about 10% by weight, of the composition; said composition being reconstitutable in a parenterally acceptable liquid.

16. The composition of claim 15 wherein said AHS comprises ferric hydroxide sucrose complex, sodium ferric gluconate complex or ferric saccharate complex.

17. The composition of claim 16 wherein the complex comprises sodium ferric gluconate complex.

18. The composition of claim 16 wherein the complex comprises ferric hydroxide sucrose complex.

19. The composition of claim 16 wherein the complex comprises ferric saccharate complex.

20. The composition of claim 15 consisting essentially of AHS and buffering agent.

21. The composition of claim 15 wherein the buffering agent comprises sodium phosphate, potassium phosphate, sodium citrate, potassium citrate, monoethanolamine, diethanolamine, triethanolamines, tromethamine or a mixture of two or more thereof.

22. The composition of claim 15 in admixture with an aqueous carrier or solvent.

23. The composition of claim 22 wherein the aqueous carrier or solvent further comprises sodium chloride, a preservative or both sodium chloride and a preservative.

* * * * *

UNITED STATES PATENT AND TRADEMARK OFFICE
CERTIFICATE OF CORRECTION

| | | |
|---|---|---|
| PATENT NO. | : 7,883,897 B2 | Page 1 of 1 |
| APPLICATION NO. | : 12/712394 | |
| DATED | : February 8, 2011 | |
| INVENTOR(S) | : Robert A. Beck and Robert A. Mateer, Jr. | |

It is certified that error appears in the above-identified patent and that said Letters Patent is hereby corrected as shown below:

On Title page, item (54), title of patent, "IRON-SACCHARADIC" should read "IRON-SACCHARIDIC"

At column 1, line 2, "IRON-SACCHARADIC" should read "IRON-SACCHARIDIC"

Signed and Sealed this
Fourteenth Day of February, 2012

David J. Kappos
*Director of the United States Patent and Trademark Office*